(12) United States Patent
Ghaffari et al.

(10) Patent No.: US 10,532,211 B2
(45) Date of Patent: Jan. 14, 2020

(54) METHOD AND SYSTEM FOR NEUROMODULATION AND STIMULATION

(71) Applicant: MC10, Inc., Lexington, MA (US)

(72) Inventors: Roozbeh Ghaffari, Cambridge, MA (US); Shyamal Patel, Somerville, MA (US); Milan Raj, Cambridge, MA (US); Ryan McGinnis, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 0 days.

(21) Appl. No.: 15/286,129

(22) Filed: Oct. 5, 2016

(65) Prior Publication Data

US 2017/0095670 A1    Apr. 6, 2017

Related U.S. Application Data

(60) Provisional application No. 62/237,214, filed on Oct. 5, 2015.

(51) Int. Cl.
*A61N 1/36* (2006.01)
*A61B 5/00* (2006.01)
(Continued)

(52) U.S. Cl.
CPC ........ *A61N 1/36139* (2013.01); *A61B 5/0024* (2013.01); *A61B 5/01* (2013.01);
(Continued)

(58) Field of Classification Search
USPC ......................................................... 607/62
See application file for complete search history.

(56) References Cited

U.S. PATENT DOCUMENTS 3,716,861 A    2/1973  Root
3,805,427 A    4/1974  Epstein
(Continued)

FOREIGN PATENT DOCUMENTS

CN        202068986 U    12/2011
DE   10 2007 046 886 A1    4/2009
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — Nicole F Lavert
*Assistant Examiner* — Nicole F Johnson
(74) *Attorney, Agent, or Firm* — Nixon Peabody LLP

(57) ABSTRACT

A system for controlling a therapeutic device and/or environmental parameters can include one or more body worn sensor devices that detect and report one or more physical, physiological, or biological parameters of a person in an environment. The sensor devices can communicate sensor data indicative of the one or more physical, physiological, or biological parameters of a person to an external hub that processes the data and communicates with the therapeutic device to provide a therapy (e.g., neuromodulation, neurostimulation, or drug delivery) as a function of the sensor data. In some embodiments, the therapeutic device can be implanted in the person. In some embodiments, the therapeutic device can be in contact with the skin of the person. The sensor devices can also communicate to the hub that communicates with one or more devices to change the environment as a function of the sensor data.

14 Claims, 5 Drawing Sheets

(51) Int. Cl.

| | |
|---|---|
| *A63B 24/00* | (2006.01) |
| *G16H 50/20* | (2018.01) |
| *G16H 20/70* | (2018.01) |
| *G16H 40/63* | (2018.01) |
| *G16H 20/30* | (2018.01) |
| *G16H 40/67* | (2018.01) |
| *A63B 22/02* | (2006.01) |
| *A61B 5/01* | (2006.01) |
| *A61B 5/021* | (2006.01) |
| *A61B 5/024* | (2006.01) |
| *A61B 5/08* | (2006.01) |
| *A61B 5/11* | (2006.01) |
| *A61M 5/172* | (2006.01) |
| *A61M 21/02* | (2006.01) |
| *A61N 7/00* | (2006.01) |
| *A63B 22/00* | (2006.01) |
| *A63B 22/04* | (2006.01) |
| *A61M 21/00* | (2006.01) |
| *A61B 5/04* | (2006.01) |
| *A61M 5/142* | (2006.01) |
| *A61B 5/053* | (2006.01) |
| *A63B 71/00* | (2006.01) |
| *A61B 5/0488* | (2006.01) |
| *A63B 22/06* | (2006.01) |
| *A63B 71/06* | (2006.01) |
| *A61F 7/00* | (2006.01) |
| *A61N 5/06* | (2006.01) |

(52) U.S. Cl.
CPC ............ *A61B 5/021* (2013.01); *A61B 5/024* (2013.01); *A61B 5/02405* (2013.01); *A61B 5/0816* (2013.01); *A61B 5/112* (2013.01); *A61B 5/1118* (2013.01); *A61B 5/4815* (2013.01); *A61B 5/4836* (2013.01); *A61M 5/1723* (2013.01); *A61M 21/02* (2013.01); *A61N 1/36067* (2013.01); *A61N 1/36071* (2013.01); *A61N 1/36114* (2013.01); *A61N 1/36117* (2013.01); *A61N 7/00* (2013.01); *A63B 22/0023* (2013.01); *A63B 22/025* (2015.10); *A63B 22/04* (2013.01); *A63B 24/0062* (2013.01); *A63B 24/0075* (2013.01); *A63B 24/0087* (2013.01); *G16H 20/30* (2018.01); *G16H 20/70* (2018.01); *G16H 40/63* (2018.01); *G16H 40/67* (2018.01); *G16H 50/20* (2018.01); *A61B 5/02438* (2013.01); *A61B 5/04004* (2013.01); *A61B 5/0488* (2013.01); *A61B 5/0533* (2013.01); *A61B 5/7275* (2013.01); *A61B 2560/0242* (2013.01); *A61F 7/00* (2013.01); *A61M 5/14276* (2013.01); *A61M 2021/0027* (2013.01); *A61M 2021/0044* (2013.01); *A61M 2021/0066* (2013.01); *A61M 2205/3523* (2013.01); *A61M 2205/3553* (2013.01); *A61M 2205/3584* (2013.01); *A61M 2205/8243* (2013.01); *A61M 2230/06* (2013.01); *A61M 2230/30* (2013.01); *A61M 2230/42* (2013.01); *A61M 2230/50* (2013.01); *A61M 2230/60* (2013.01); *A61M 2230/62* (2013.01); *A61M 2230/65* (2013.01); *A61N 5/0622* (2013.01); *A63B 22/0076* (2013.01); *A63B 22/02* (2013.01); *A63B 22/0605* (2013.01); *A63B 22/0664* (2013.01); *A63B 2024/0065* (2013.01); *A63B 2024/0078* (2013.01); *A63B 2024/0093* (2013.01); *A63B 2071/0081* (2013.01); *A63B 2071/0625* (2013.01); *A63B 2220/18* (2013.01); *A63B 2220/30* (2013.01); *A63B 2220/40* (2013.01); *A63B 2220/805* (2013.01); *A63B 2225/20* (2013.01); *A63B 2225/50* (2013.01); *A63B 2230/045* (2013.01); *A63B 2230/06* (2013.01); *A63B 2230/062* (2013.01); *A63B 2230/10* (2013.01); *A63B 2230/42* (2013.01); *A63B 2230/425* (2013.01); *A63B 2230/50* (2013.01); *A63B 2230/60* (2013.01)

(56) References Cited

U.S. PATENT DOCUMENTS

| | | | |
|---|---|---|---|
| 3,838,240 | A | 9/1974 | Schelhorn |
| 4,278,474 | A | 7/1981 | Blakeslee |
| 4,304,235 | A | 12/1981 | Kaufman |
| 4,416,288 | A | 11/1983 | Freeman |
| 4,658,153 | A | 4/1987 | Brosh |
| 4,911,169 | A | 3/1990 | Ferrari |
| 5,059,424 | A | 10/1991 | Cartmell |
| 5,272,375 | A | 12/1993 | Belopolsky |
| 5,306,917 | A | 4/1994 | Black |
| 5,326,521 | A | 7/1994 | East |
| 5,331,966 | A | 7/1994 | Bennett |
| 5,360,987 | A | 11/1994 | Shibib |
| 5,471,982 | A | 5/1995 | Edwards |
| 5,454,270 | A | 10/1995 | Brown |
| 5,491,651 | A | 2/1996 | Janic |
| 5,567,975 | A | 10/1996 | Walsh |
| 5,580,794 | A | 12/1996 | Allen |
| 5,617,870 | A | 4/1997 | Hastings |
| 5,811,790 | A | 9/1998 | Endo |
| 5,817,008 | A | 10/1998 | Rafert |
| 5,907,477 | A | 5/1999 | Tuttle |
| 6,063,046 | A | 5/2000 | Allum |
| 6,220,916 | B1 | 4/2001 | Bart |
| 6,265,090 | B1 | 7/2001 | Nishide |
| 6,282,960 | B1 | 9/2001 | Samuels |
| 6,343,514 | B1 | 2/2002 | Smith |
| 6,387,052 | B1 | 5/2002 | Quinn |
| 6,410,971 | B1 | 6/2002 | Otey |
| 6,421,016 | B1 | 7/2002 | Phillips |
| 6,450,026 | B1 | 9/2002 | Desarnaud |
| 6,455,931 | B1 | 9/2002 | Hamilton |
| 6,567,158 | B1 | 5/2003 | Falcial |
| 6,626,940 | B2 | 9/2003 | Crowley |
| 6,628,987 | B1 | 9/2003 | Hill |
| 6,641,860 | B1 | 11/2003 | Kaiserman |
| 6,775,906 | B1 | 8/2004 | Silverbrook |
| 6,784,844 | B1 | 8/2004 | Boakes |
| 6,965,160 | B2 | 11/2005 | Cobbley |
| 6,987,314 | B1 | 1/2006 | Yoshida |
| 7,259,030 | B2 | 8/2007 | Daniels |
| 7,265,298 | B2 | 9/2007 | Maghribi |
| 7,302,751 | B2 | 12/2007 | Hamburgen |
| 7,337,012 | B2 | 2/2008 | Maghribi |
| 7,487,587 | B2 | 2/2009 | Vanfleteren |
| 7,491,892 | B2 | 2/2009 | Wagner |
| 7,521,292 | B2 | 4/2009 | Rogers |
| 7,557,367 | B2 | 7/2009 | Rogers |
| 7,618,260 | B2 | 11/2009 | Daniel |
| 7,622,367 | B1 | 11/2009 | Nuzzo |
| 7,727,228 | B2 | 6/2010 | Abboud |
| 7,739,791 | B2 | 6/2010 | Brandenburg |
| 7,759,167 | B2 | 7/2010 | Vanfleteren |
| 7,815,095 | B2 | 10/2010 | Fujisawa |
| 7,960,246 | B2 | 6/2011 | Flamand |
| 7,982,296 | B2 | 7/2011 | Nuzzo |
| 8,097,926 | B2 | 1/2012 | De Graff |
| 8,198,621 | B2 | 6/2012 | Rogers |
| 8,207,473 | B2 | 6/2012 | Axisa |
| 8,217,381 | B2 | 7/2012 | Rogers |
| 8,332,053 | B1 | 12/2012 | Patterson |
| 8,372,726 | B2 | 2/2013 | De Graff |
| 8,389,862 | B2 | 3/2013 | Arora |
| 8,431,828 | B2 | 4/2013 | Vanfleteren |

(56) References Cited

U.S. PATENT DOCUMENTS

| | | |
|---|---|---|
| 8,440,546 B2 | 5/2013 | Nuzzo |
| 8,536,667 B2 | 9/2013 | De Graff |
| 8,552,299 B2 | 10/2013 | Rogers |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,320,907 B2 | 4/2016 | Bogie |
| 9,324,733 B2 | 4/2016 | Rogers |
| 9,372,123 B2 | 6/2016 | Li |
| 9,408,305 B2 | 8/2016 | Hsu |
| 9,515,025 B2 | 12/2016 | Rogers |
| 9,516,758 B2 | 12/2016 | Arora |
| 9,545,216 B2 | 1/2017 | D'Angelo |
| 9,545,285 B2 | 1/2017 | Ghaffari |
| 9,554,850 B2 | 1/2017 | Lee |
| 2001/0012918 A1 | 8/2001 | Swanson |
| 2001/0021867 A1 | 9/2001 | Kordis |
| 2002/0000813 A1 | 1/2002 | Hirono |
| 2002/0026127 A1 | 2/2002 | Balbierz |
| 2002/0082515 A1 | 6/2002 | Campbell |
| 2002/0094701 A1 | 7/2002 | Biegelsen |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2002/0173730 A1 | 11/2002 | Pottgen |
| 2002/0193724 A1 | 12/2002 | Stebbings |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0029680 A1 | 2/2005 | Jung |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0248312 A1 | 11/2005 | Cao |
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0179373 A1 | 8/2007 | Pronovost |
| 2007/0190880 A1 | 8/2007 | Dubrow |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0030167 A1 | 2/2010 | Thirstrup |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |

(56) References Cited

U.S. PATENT DOCUMENTS

| | | |
|---|---|---|
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034760 A1* | 2/2011 | Brynelsen ............ A61B 5/1118 600/37 |
| 2011/0034912 A1 | 2/2011 | De Graff |
| 2011/0051384 A1 | 3/2011 | Kriechbaum |
| 2011/0054583 A1 | 3/2011 | Litt |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0140856 A1 | 6/2011 | Downie |
| 2011/0140897 A1 | 6/2011 | Purks |
| 2011/0175735 A1 | 7/2011 | Forster |
| 2011/0184320 A1 | 7/2011 | Shipps |
| 2011/0185611 A1 | 8/2011 | Adams |
| 2011/0213559 A1 | 9/2011 | Pollack |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0222375 A1 | 9/2011 | Tsubata |
| 2011/0263950 A1 | 10/2011 | Larson |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0150072 A1 | 6/2012 | Revol-Cavalier |
| 2012/0157804 A1 | 6/2012 | Rogers |
| 2012/0172697 A1 | 7/2012 | Urman |
| 2012/0178367 A1 | 7/2012 | Matsumoto |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0044215 A1 | 2/2013 | Rothkopf |
| 2013/0085552 A1 | 4/2013 | Mandel |
| 2013/0095459 A1* | 4/2013 | Tran ............... A61B 5/6816 434/247 |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0150693 A1 | 6/2013 | D'angelo |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0253285 A1 | 9/2013 | Bly |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0328219 A1 | 12/2013 | Chau |
| 2013/0331914 A1 | 12/2013 | Lee |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0240932 A1 | 8/2014 | Hsu |
| 2014/0249520 A1 | 9/2014 | Ghaffari |
| 2014/0257427 A1 | 9/2014 | Marnfeldt |
| 2014/0303452 A1 | 10/2014 | Ghaffari |
| 2014/0303680 A1 | 10/2014 | Donnelly |
| 2014/0308930 A1 | 10/2014 | Tran |
| 2014/0316192 A1 | 10/2014 | De Zambotti |
| 2014/0318699 A1* | 10/2014 | Longinotti-Buitoni ................ A61B 5/0002 156/247 |
| 2014/0340857 A1 | 11/2014 | Hsu |
| 2014/0371547 A1 | 12/2014 | Gartenberg |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Fastert |
| 2015/0342036 A1 | 11/2015 | Elolampi |
| 2016/0015962 A1 | 1/2016 | Shokoueinejad Maragheh |
| 2016/0027834 A1 | 1/2016 | de Graff |
| 2016/0045162 A1 | 2/2016 | De Graff |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |
| 2016/0338646 A1 | 11/2016 | Lee |
| 2016/0361015 A1 | 12/2016 | Wang |
| 2016/0371957 A1 | 12/2016 | Ghaffari |

(56) References Cited

U.S. PATENT DOCUMENTS

| | | | |
|---|---|---|---|
| 2016/0381789 A1 | 12/2016 | Rogers | |
| 2017/0019988 A1 | 1/2017 | McGrane | |

FOREIGN PATENT DOCUMENTS

| | | |
|---|---|---|
| EP | 0585670 A2 | 3/1994 |
| EP | 0779059 A1 | 6/1997 |
| EP | 1808124 A2 | 7/2007 |
| EP | 2259062 A2 | 12/2010 |
| JP | 05-087511 A | 4/1993 |
| JP | 2005-052212 A | 3/2005 |
| JP | 2009-170173 A | 7/2009 |
| WO | WO 1999/038211 A2 | 7/1999 |
| WO | WO 2003/021679 A2 | 3/2003 |
| WO | WO 2005/083546 A1 | 9/2005 |
| WO | WO 2005/122285 A2 | 12/2005 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2015/145471 A1 | 10/2015 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |
| WO | WO 2016/205385 A1 | 12/2016 |
| WO | WO 2017/015000 A1 | 1/2017 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Wikipedia, "Ball bonding" article [online]. Cited in PCT/US2015/051210 search report dated Mar. 1, 2016 with the following information "Jun. 15, 2011 [retrieved on Nov. 15, 2015}. Retrieved 12-18, 29 from the Internet: <URL: https://web.archive.org/web/20110615221003/hltp://en.wikipedia.org/wiki/Ball_bonding>., entire document, especially para 1, 4, 5, 6," 2 pages, last page says ("last modified on May 11, 2011").

Bossuyt et al., "Stretchable Electronics Technology for Large Area Applications: Fabrication and Mechanical Characterizations", vol. 3, pp. 229-235 (7 pages) (Feb. 2013).

Jones et al., "Stretchable Interconnects for Elastic Electronic Surfaces". vol. 93, pp. 1459-1467 (9 pages) (Aug. 2005).

Lin et al., "Design and Fabrication of Large-Area, Redundant, Stretchable Interconnect Meshes Using Excimer Laser Photoablation and In Situ Masking", (10 pages) (Aug. 2010).

Kim et al., "A Biaxial Stretchable Interconnect with Liquid-Alloy-Covered Joints on Elastomeric Substrate", vol. 18, pp. 138-146 (9 pages) (Feb. 2009).

(56) References Cited

OTHER PUBLICATIONS

Extended European Search Report for Application No. EP 16854252. 0, dated Apr. 24, 2019 (8 pages).

* cited by examiner

METHOD AND SYSTEM FOR NEUROMODULATION AND STIMULATION

CROSS-REFERENCE TO RELATED APPLICATIONS

This application claims any and all benefits as provided by law including benefit under 35 U.S.C. § 119(e) of the U.S. Provisional Application No. 62/237,214, filed Oct. 5, 2015, the contents of which are incorporated herein by reference in its entirety

STATEMENT REGARDING FEDERALLY SPONSORED RESEARCH

Not Applicable

REFERENCE TO MICROFICHE APPENDIX

Not Applicable

BACKGROUND

Technical Field of the Invention

The present invention is directed to methods and systems for monitoring physical, physiologic and/or biologic information about one or more persons or subjects and using physical, physiologic and/or biologic information or information derived from physical, physiologic and/or biologic information, to interact with therapeutic devices and/or environmental systems and devices. More specifically, the system can include one or more sensors that detect a condition of one or more persons or subjects and use that information to change the operation of the system or a device in communication with the system.

Description of the Prior Art

Many of the existing health and wellness aides utilize sensors to detect and record various physical and physiologic information about a person or a subject. These devices use sensors, such as accelerometers, to measure movement and store this information for later presentation in various forms to the person wearing the device or other person, such as their coach. These devices assist in training by enabling the user to review historic information and use this information to make subsequent decisions.

Other systems utilize body worn or carried devices to provide some form of convenient environmental control. The systems, typically referred to as Home Automation, utilize information available from a smart phone or similar device to automate some control of the home environment. For example, some thermostats include sensors that detect the presence or absence of people in a room or zone and attempt to reduce energy costs by automatically reducing the heating or cooling of the zone until activity is detected. Other thermostat systems can use the location information available from a smart phone to determine when and how to control the heating and cooling of a home. When, the system detects that the person is away from home, the thermostat automatically turns the heating or cooling system down or off until the person moves within a predefined distance to the home, at which point the thermostat turns the heating or cooling system on to make the home comfortable for the person's arrival.

SUMMARY

The present invention is directed to systems that are adapted to modify the operation or condition of one or more environments (or systems that control or influence the state of one or more environment conditions) or systems that control the operation of a device, as a function of one or more sensed conditions of one or more people or subjects (which includes animals and inanimate objects). The present invention is directed to methods for monitoring physical, physiologic and/or biologic conditions of a person or subject and using this information, either alone or in combination with other information, to influence or control, either directly or indirectly, one or more environmental factors (e.g., heating, cooling, humidity, light) or the operation of a system, or a device (e.g., providing electrical stimulation, photostimulation, thermal stimulation neurostimulation, ultra sound stimulation, and/or drug delivery).

In accordance with the invention, one or more people and/or subjects can be monitored by one or more sensing devices that indicate one or more conditions of some or all of the people and/or subjects. The conditions can include physical conditions, such as location and motion of the person or subject or a part (e.g., arm, leg, hand, foot or head) of the person or subject. The conditions can include physiologic or biologic conditions, such as the mechanical, physical, thermal, biological and/or biochemical aspects of functions and/or processes of the person or subject. The conditions can include mental, emotional, and psychiatric conditions, such as, mood, focus, concentration, depression, and alertness determined as function of the mechanical, physical, thermal, biological and/or biochemical sensed conditions.

The sensed condition information about one or more persons or subjects can be collected and processed or analyzed and used as an input or used to select or modify an input to a control system that controls the person or subject's environment, or a machine or device related to the person or subject (e.g., providing treatment or therapy).

The system can utilize one or more algorithms (e.g. computer programs, functions or processes) to determine whether to modify the environment or the operation of a system or a device. For example, the algorithm can utilize data characterizing the condition (e.g., motion information such as speed, velocity, or acceleration, temperature, ExG signals) as an input to a function or a control system that controls at least a portion of the operation of a system or device. In another example, the algorithm can compare one or more parameters representative of one or more sensed conditions to a predefined threshold value (or range) and based on the outcome of the comparison, take no further action or proceed to interact with a control system to cause a change in an environment or the operation of the device. In accordance with some embodiments of the invention, the system can utilize one or more algorithms to determine or select an algorithm for controlling changes in the environment (e.g., a summer or winter control algorithm) or to determine an algorithm for controlling the operation of a device (e.g., a mild condition neurostimulation algorithm, a severe condition neurostimulation algorithm, a daytime neurostimulation algorithm, or a nighttime neurostimulation algorithm). These algorithms are also referred to as operation profiles.

In accordance with some embodiments, the system, according to one or more algorithms, can include additional data as inputs to determine whether to interact with the control system to cause a change in an environment or the operation of a system or a device. The additional data can include data obtained from local and/or remote sources, such as environmental data (e.g., temperature, barometric pressure, humidity, wind velocity and wind direction), time of day, ambient noise levels (e.g., levels of music playing or background noise), and ambient light levels (e.g., time of day, whether lights are on, whether is sunny or cloudy outside). The system can process these data values using a logic tree or a set of rules to determine whether to interact with the control system to cause a change in an environment or the operation of a device.

In accordance with some embodiments of the invention, the system, according to one or more algorithms, can determine a trend or a rate of change of one or more parameters and use the rate of change to predict an event time in the future when a specific parameter could exceed a threshold and require intervention. The system can also check the parameter one or more times prior to the event time to confirm that the rate of change of the specific parameter has not changed and the event time does not need to be changed. Where the rate of change of the parameter has changed, the event time can be re-calculated using the new rate of change or as a function of two or more previously determined rates of change. In accordance with some embodiments of the invention, the system can interact with the control system prior to the event time, in order to cause a change in the environment or the operation of the device prior to the specific parameter coming close to the threshold level.

In accordance with some embodiments, the system can determine a measure of degree to which the control system can change the environment or the operation of the device. For example, the system can determine the number of degrees to increase or decrease the set-point temperature of thermostat to cause an increase or decrease in the environmental temperature by a predetermine time, instead of simply increasing the temperature by a predefined value (e.g., raise the temperature 5 degrees) and then monitoring a set of conditions to determine whether to increase or decrease the temperature at a later time. In accordance with some embodiments of the invention, the system can take into consideration the operational characteristics of the system, or device being controlled. In accordance with some embodiments of the invention, the system can provide information wirelessly about biometrics, body movement, and physiology to an implanted device (e.g. pacemaker, deep brain stimulator, vagus nerve stimulator, tibial nerve stimulator, spinal cord stimulators, peripheral nerve stimulators, transcranial magnetic stimulators, drug infusion pumps), which in turn, can tune its mode of operation based on this information. For example, for a deep brain stimulation device, the amount of electrical current and stimulus frequency can be determined and adjusted as a function of the amount of tremor recorded by the wearable system. The settings that give rise to the lowest prevalence of tremors can be preferentially programmed as part of the feedback loop. In another example, for a thermostat, the amount of time needed to heat up or cool down the room to a specific temperature given the existing environmental conditions can be determined so that the heating or cooling action can be initiated prior to the event deadline, so the desired temperature occurs at or before the event deadline. Similarly, for a motor vehicle, the system can determine the time to initiate the turn (e.g., to avoid hitting an obstacle) or initiate stopping (e.g., to account for stopping distance due to road conditions).

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

DETAILED DESCRIPTION OF PREFERRED EMBODIMENTS

Figure 1:
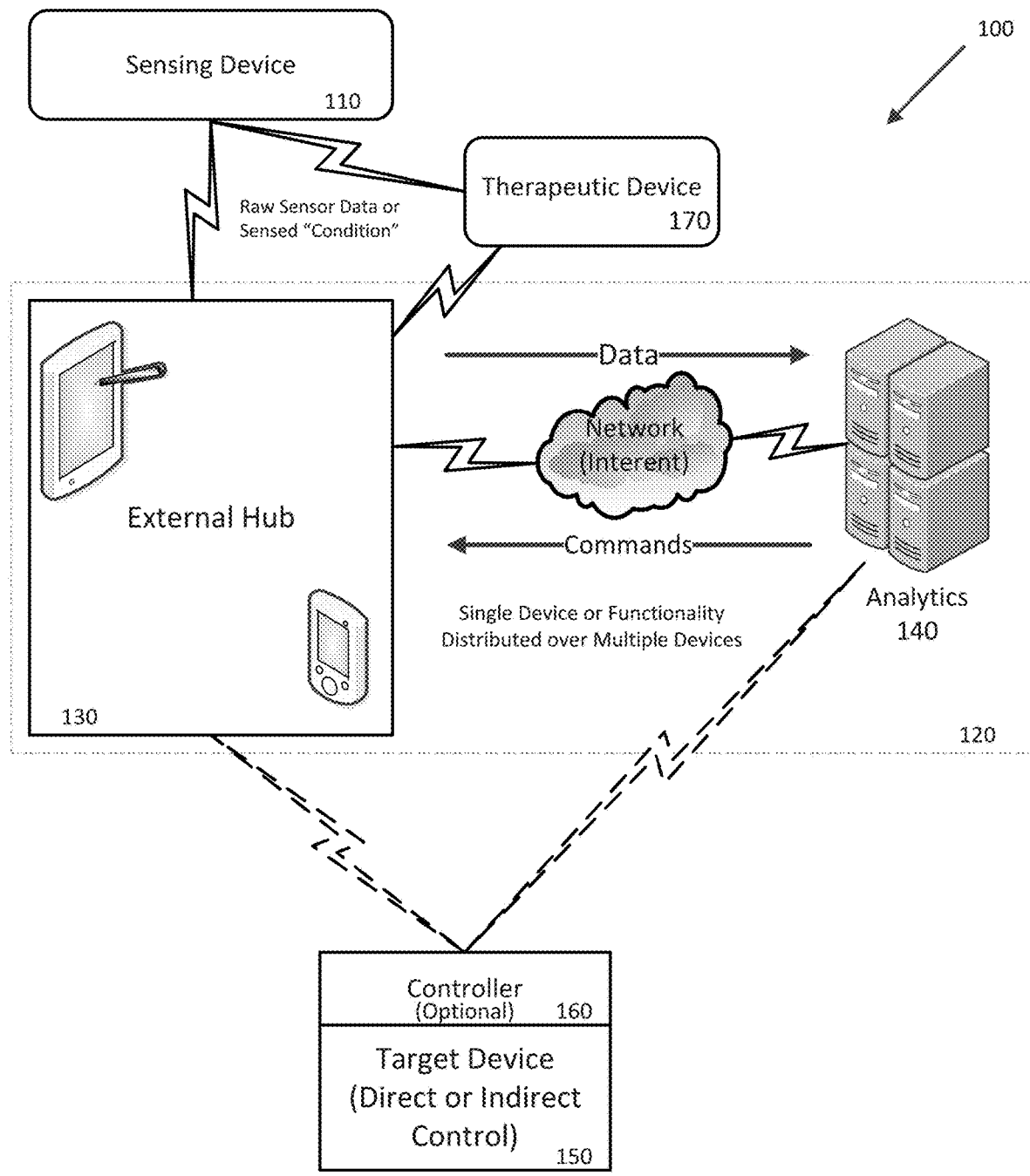
FIG. 1 is a block diagram of a system according to some embodiments of the invention.

The present invention is directed to systems and methods for modifying the operation or condition of one or more environments or systems as function of one or more sensed conditions of one or more people or subjects. In accordance with the invention, one or more people and/or subjects can be monitored by one or more sensing devices that indicate one or more conditions of some or all of the people and/or subjects. The conditions can include physical conditions, such as location and motion of the person or subject or a part of the person or subject. The conditions can include physiologic or biologic conditions, such as the mechanical, physical, thermal and/or biochemical aspects of the biologic and physiologic functions and/or processes of the person or subject.

In accordance with some embodiments of the invention, the sensed condition information can be used to modify the operation of the system (e.g., a device or set of devices), for example, to cause a computer program, function or process to be executed or to change the flow of an executing program, function or process. In one example, a motion sensor (e.g., an accelerometer) could detect motion characteristic of running or walking and as a result, the system could cause a step tracking computer program, function or process to be executed to count the number of steps taken and/or the distance traveled.

In accordance with some embodiments of the invention, the sensed condition information can be used to modify the operation of the system (e.g., a device or set of devices), for example, to cause other sensors to be activated so that their data can be used as part of newly started or an ongoing computer program, function or process for monitoring the person or subject. In one example, a temperature sensor could detect a rise in the person or subject's temperature (e.g., above threshold or steady state body temperature) and as a result, the system could activate sensors to detect heart rate (e.g., EKG) and/or respiration and as a result, begin to monitor heart rate and/or respiration as part of a newly started or ongoing health monitoring program, function or process. Similarly, the rise in temperature above the designated threshold could trigger a device (e.g., a therapeutic device in contact with a tissue of the person or subject) to reconfigure itself from idle mode to stimulatory mode based on wireless signal transmission from the temperature sensor to the therapeutic device.

In accordance with some embodiments of the invention, the sensed condition information can be used to cause the system (e.g., a device or set of devices) to communicate with one or more other systems, resulting in a change in operation of these other systems. For example, the system can send a signal (e.g., wired or wireless) to a remote system and the signal can cause the remote system to change its operation or the operation of a system under its control (e.g. an implantable device such as a pacemaker or a deep brain or spinal cord stimulator, or a wearable device such as a skin-mounted stimulation or drug delivery device). In another example, the system can detect or predict a problematic temperature change (e.g., up or down to an unsafe level or range) in the person or subject and the system can send a signal to a thermostat and the thermostat can cause a heating or cooling system to turn on or off or change the temperature in the environment to offset the detected or predicted temperature.

FIG. 1 shows an example of a system 100 according to some embodiments of the invention. In this embodiment, the system 100 can include one or more sensing devices 110, an external hub 130, and one or more therapeutic devices 170. The one or more sensing devices 110 can transmit sensor data or one or more sensed conditions to the external hub 130. In accordance with some embodiments, the external hub 130 can communicate with the therapeutic device 170 and cause the therapeutic device 170 to change its operation as a function of the sensor data or one or more of the sensed conditions. In accordance with some embodiments, the one or more sensing devices 110 can communicate directly with the therapeutic device 170 and cause the therapeutic device 170 to change its operation as a function of the sensor data or one or more of the sensed conditions. For example, the sensor data can indicate a person's skin temperature and determine a measure of core body temperature from the skin temperature. Galvanic skin response and other measures of perspiration can be used to determine heat loss and further estimate core body temperature or estimate changes in core body temperature. By monitoring skin temperature over time, the sensing device 110 can determine trends and predict or anticipate when a person's body temperature will rise above or drop below a predefined threshold (e.g., a dangerous condition). This trend information can be used to control the environmental control systems to select a rate of change (e.g., of heating or cooling) that is better suited to meet the desired goals of the system (e.g., to lower or raise the person's body temperature by cooling or heating the environment). Further, the sensing device 110 can continue to monitor skin temperature and continuously adjust the environmental temperature as function of the person's skin temperature or core body temperature.

An optional analytics system 140 can also be connected to the system 100. In accordance with some embodiments, the analytics system 140 can be integrated with the external hub 130 as an integrated system 120 in which the functionality of external hub 130 and the analytics system 140 are provided by an integrated system 120 or operate in the system as if they are part of an integrated system 120. In accordance with some embodiments of the invention, the external hub 130 and analytics system 140 can be separate systems connected by a network such as the internet. The analytics system 140 can communicate with the external hub 130. For example, the analytics system 140 can receive data (e.g. sensor data or condition information) from the external hub 130, e.g., via a network such as the internet. The analytics system 140 can also provide commands to the external hub 130. The external hub 130 can send commands to the sensing device 110 and the sensing device 110 can send commands to the therapeutic device 170.

In accordance with some embodiments of the invention, the system 100 can optionally comprise a target device 150 and/or controller 160. The controller 160 can be connected to and used to control the target device 150, directly or indirectly.

The sensing device 110 can be any device capable of detecting or measuring physical, physiologic or biologic functions and more than one sensing device can be included in the system 100. Each sensing device 110 can be configured with one or more controllers or microcontrollers, such as a low power system on a chip microcontroller, associated memory and a power source, such as a battery. The controller can be configured to run one or more digital signal processing algorithms and/or raw data signal processing algorithms. Each sensing device 110 can include one or more sensors such as accelerometers, gyroscopes, temperature sensors, galvanic skin responses sensors, chemical sensors, light sensors (e.g., visible or invisible light), sound sensors, bio-potential electrodes (e.g., ExG, such as ECG, EMG, EEG), and other sensors. Each sensing device 110 can be configured to send sensor data to the external hub 130. The sensor data can include raw sensor signal data, processed sensor signal data (e.g. filtered, scaled, segmented), signal features (e.g. dominant frequency, range, root mean square value) and algorithm output (e.g. fall detection alarm, tremor score, sleep quality, posture quality). The sensor data can include other information, such as metadata (e.g., information about the sensor device, the date, the time, the type and the scale or units of the sensor data). The sensing devices can be placed on the head, the chest, the arms, the hands, the legs, the feet and torso of the person or subject.

Some examples of sensors and types of sensor data include, but are not limited to, dry and gel-enhanced electrodes and electrode arrays for measuring electrocardiogram (ECG) waveforms, heart rate, heart rate variability, electromyography (EMG) from distinct muscle groups (e.g. tibialis anterior muscle), electroencephalograms (EEG), electrooculagrams, skin conductivity and galvanic skin response; Strain gauges for measuring pulse waveforms from superficial arteries and respiration patterns; Piezoelectric sensors and actuators for mechanical energy harvesting and pulse waveform measurements; Temperature sensors, such as thermal couples and thermistors (for measuring core and skin surface temperature), optical sensors and/or photodetectors (for ultraviolet, visible light analysis, and/or colorimetry analysis), pH sensor, bioanalyte sensor (e.g. potassium, sodium, calcium, glucose, hormones, proteins), chemical/gas sensor (pollutants, deadly gases, mercury), microfluidic sensors for capturing and analyzing (e.g., composition and volume) skin secretions including perspiration and oils. Other sensor data can include derivative sensor data derived (e.g., derivative data) from the raw sensor data over time or frequency.

The processed sensor data can be derived from the raw sensor data by various well known processes to remove noise or to characterize sets or units of raw sensor data (e.g., into features, tokens and/or messages). The sensing device 110 can include a processor and associated memory and execute one or more computer programs that collect sensor data on a periodic basis. The sensing device 110 can include a communication system that enables the raw sensor data or the processed sensor data to be transmitted to a remote device or system, such as the external hub 130. The communication system can be adapted to provide wired or wireless communication with a remote device, such as the external hub 130.

Each sensing device 110 can take many forms, including, for example, a flexible or stretchable conformable sensing device that can be adhered to the skin, a bracelet or strap that can be worn on the body, an article of clothing or a pad or plate that can be positioned against or adjacent the body. The sensing device 110 can detect and measure the physical motion of the person or subject. The sensing device 110 can detect and measure temperature such as ambient environmental temperature as well as the temperature of the person or subject (e.g., core body and/or skin surface). The sensing device 110 can detect and measure the pulse, blood pressure, galvanic skin response, and/or blood oxygen of the person or subject. The sensing device 110 can detect and measure bio-potentials (e.g., EKG, EMG and EEG signals), strain, surface body temperature, core body temperature, salt concentrations in sweat, sweat loss rate, blood micronutrient levels, glucose concentration in sweat, visible/infrared/ultraviolet radiation, contact pressure, barometric pressure, skin strain, skin modulus, images of sub-dermal structures using ultrasound transducers from the person or subject. The sensing device 110 can contain actuators to deliver electric current (electric fields) to transdermally direct nanoparticles through skin (e.g. pharmacological agents), LED arrays (e.g., UV, blue, near infrared light, or infrared) to deliver photo-activation therapy to skin.

In accordance with some embodiments of the invention, the sensing device 110 can be a skin-mounted patch, such as those described in commonly owned U.S. application Ser. No. 14/524,817, which is incorporated herein by reference.

The sensing device 110 can sample the output of one or more sensors on a periodic basis (e.g., at 1 Hz, 5 Hz, 10 Hz, 60 Hz, or more) and, if necessary, convert the signals into digital data. The digital data can be buffered, stored and streamed to one or more remote devices.

In accordance with some embodiments of the invention, the therapeutic device 170 can be in contact with a tissue of the person or subject. The tissue can be a connective tissue, a muscle tissue, a nervous tissue, an epithelial tissue, or a mineralized tissue. Examples of tissues include, but are not limited to, skin, an internal organ (e.g., brain, heart, liver, prostate, lung, kidney, gall bladder, spleen), muscle, bone, spinal cord, or cartilage.

Figure 4:
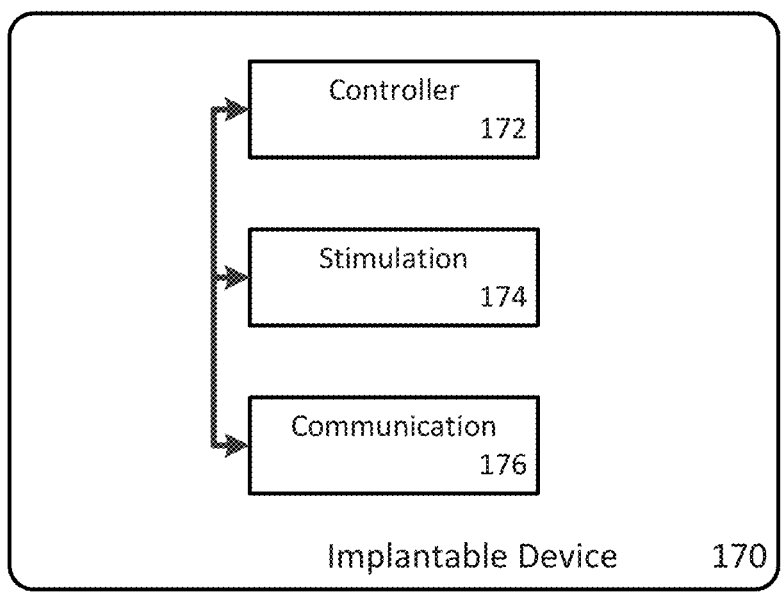
FIG. 4 is a block diagram of a therapeutic device according to some embodiments of the invention.

In accordance with some embodiments of the invention, the therapeutic device 170 can be an implantable device as shown in FIG. 4. The therapeutic device 170 can include a controller 172 that controls the operation of the device, a stimulation component 174 (e.g., a transducer, heating element, light source, electrode, energy source, ultrasonic transducer, or drug delivery device) that can be controlled by the controller 172 to apply the therapy and a communication module 176 controlled by the controller 172 for communication with external devices such as sensing device 110 and external hub 130. Examples of vendors and therapy devices include: Cerbomed (Nemos®), CerebralRx (FitNeS), Cyberonics Inc. Sorin (AspireSR®, Centro™, ProGuardian™, and Vitaria™), and Neuropace (RNS) providing vagus nerve stimulation devices for treating epilepsy. Other vagus nerve stimulation devices include electroCore (gammaCore™) for treating migraine headaches, EnteroMedics Inc. (Maestro®) for treating Obesity, Microtransponder (Vivistim®) for treating upper-limb deficit, SetPoint Medical (Setpoint platform) for treating inflammatory diseases, and Cyberonics Inc./Sorin SPA (VNS, Equilia™) for treating heart failure. Other neuromodulation therapy devices include Advanced Uro-Solutions (Nuro™ system) for modulating the tibial nerve to treat overactive bladder, Atrotech (Atrostim PNS™) for modulating the phrenic nerve to treat respiratory muscle paralysis, Autonomic Technologies (Pulsante™) for modulating the sphenopalatine ganglion to treat cluster headaches, CVRx (Barostim neo) to stimulate carotid baroreceptors to treat resistant hypertension, ImThera Medical (aura6000™) to stimulate the hypoglossal nerve to treat sleep apnea, NeuImpulse (Lightpulse 100) to stimulate peripheral nerves to treat chronic pain, nUro Inc./Nuviant Medical (Synapse™) to stimulate the tibial nerve to treat overactive bladder, Medtronic (InterStimII) for stimulating the sacral nerve to treat overactive bladder, Oculeve/Allergan plc (OD-01) to stimulate the lacrimal gland to treat dry eye conditions, SPR Therapeutics (Micropulse®) to stimulate peripheral nerves to treat chronic pain, and Uroplasty Inc. (Urgent® PC) to stimulate the tibial and sacral nerves to treat overactive bladder; Neuromodulation therapy devices for modulating the spinal cord to treat chronic pain include Boston Scientific (Precision Spectra™, Illumina 3D™ software), Bioness Inc. (StimRouter™), Medtronic (RestoreSensor, Intellis RC™), Nevro Corp (Senza), and St. Jude Medical (Protégé, Proclaim™); Neuromodulation therapy devices for modulating the dorsal ramus nerve or dorsal root ganglion to treat chronic pain (including lower back pain) include Mainstay Medical (ReActiv8™), Spinal Modulation (Axium®), and StimWave (Freedom-4™); Deep brain modulation therapy devices for treating Parkinson's Disease include Aleva Neurotherapeutics (spiderSTIM™), Boston Scientific (Vercise™), Deep Brain Innovations (TOPS™), Medtronic (Activa® PC), Sapiens SBS Medtronic (SureStim®), St. Jude Medical (Infinity™); Deep brain modulation therapy devices for treating other diseases, such as, Alzheimer's, Epilepsy, and depression include Functional Neuromodulation (DBS-f), Medtronic (Activa® PC), NeuroSigma (eTNS™), NeuroVista Corp (implant device). The therapeutic device can also include any of the devices used in the following clinical trials: Cyberonics Inc. Sorin (Vagus Nerve Stimulation Clinical Outcomes Measured Prospectively in Patients Stimulated-NCT01281293 V-COMPAS), Cyberonics Inc. Sorin. (Autonomic Neural Regulation Therapy to Enhance Myocardial Function in Heart Failure Study-NCT01823887 ANTHEM-HF), Cyberonics Inc. Sorin (VNS Therapy Automatic Magnet Mode Outcomes Study in Epilepsy Patients Exhibiting Ictal Tachycardia-NCT01846741 E37), ElectroCore LLC (Vagus Nerve for the Treatment of Cluster Headache-NCT01792817), ImThera Medical Inc. (Targeted Hypoglossal Neurostimulation Study No. 2-NCT01796925 THN2), Mainstay Medical (ReActiv8 for Chronic Low Back Pain (ReActiv8-A)-NCT01985230), Medtronic (Stimulation of the Anterior Nucleus of the Thalamus for Epilepsy-NCT00101933 SANTE), Medtronic (A Pilot Study of Deep Brain Stimulation to the Lateral Habenulae in Treatment—Resistant Depression-NCT01798407), Medtronic (DBS for TRD Medtronic Activa PC+S—NCT01984710), Medtronic (DBS Therapy for Treatment Resistant Depression-NCT02046330), Metavention (Complement Study—A First-in-Human Study of Metabolic Neuromodulation Therapy-NCT02278068), MicroTransponder Inc. (Vagus Nerve Stimulation (VNS) with Rehabilitation for Upper Limb Function Improvement After Stroke-NCT01669161 VIVISTIM), Scion NeuroStim (A Non-Invasive Neuromodulation Device for Treatment of Migraine Headache-NCT01899040), Scion NeuroStim (The Effects of Neuromodulation on Glucose Metabolism in Type 2 Diabetes-NCT02130401), Scion NeuroStim (Caloric Vestibular Stimulation-NCT02134795), Spinal Modulation (A Multi-Centre RCT of the Axium® Neurostimulator for the Treatment of Chronic Inguinal Pain Following Surgery (Smashing)-NCT02349659 SMASHING), St. Jude Medical (SUNBURST (Success Using Neuromodulation with Burst) Study-NCT02011893 SUNBURST), St. Jude Medical (Chronic Pain of the Trunk and/or Limbs-NCT02143791 PRODIGY-1), Uroplasty Inc. (Prospective, Multicenter Trial to Investigate the Safety and Efficacy of Percutaneous Tibial Nerve Stimulation for the Treatment of Fecal Incontinence-NCT01666405 URGENT-PC).

The therapeutic device 170 can be any known implantable device that can communicate with the sensing device 110 (and/or optionally, the external hub 130) and sense a condition of the person or subject from inside the body and/or apply a treatment or therapy to the body. The therapeutic device 170 can include pacemakers, deep brain stimulation devices, vagus nerve stimulators, tibial nerve stimulators, spinal cord stimulators, peripheral nerve stimulators, transcranial magnetic stimulators, and/or drug infusion pumps). The therapeutic device 170 can receive information from the sensing device 110 and change its operation (e.g., adjust the pacemaker heartbeat, adjust the level of brain or nerve stimulation, and/or adjust the drug infusion levels). The therapeutic device 170 can send information to the sensing device 110, the sensing device 110 and/or the hub 130 can analyze or process the received information and then send a command and/or data to the therapeutic device 170 that changes the operation of the therapeutic device (e.g., adjust the pacemaker heartbeat, adjust the level of brain or nerve stimulation, and/or adjust the drug infusion levels).

In accordance with some embodiments of the invention, the therapeutic device 170 can also be digested by the person or subject so that the therapeutic device is in contact with the digestive tract of the person or subject.

In accordance with some embodiments of the invention, the therapeutic device 170 can also be in contact with the skin of the person or subject. For example, the therapeutic device 170 can be any known wearable device that can communicate with the sensing device 110 (and/or optionally, the external hub 130) and sense a condition of the person or subject and/or apply a treatment or therapy to the body. Examples of wearable devices can be in the form of a watch, a wristband, a patch, or glasses. The wearable device can also be embedded in a garment worn by the person or subject. The device can provide stimulation to a portion of the body of the person or subject (e.g., brain, breast) or deliver a drug transdermally (e.g., IontoPatch 80 Transdermal Drug Delivery System, W. St. Paul, Minn.)

The therapeutic device 170 can be a therapeutic device adapted to apply a treatment or therapy to the person or subject. The therapeutic device 170 can comprise an electric and/or chemical actuator or stimulator. In some embodiments, the therapeutic device 170 can apply electric pulses, e.g., for neurostimulation or pain management. In some embodiments, the therapeutic device 170 can apply ultrasound, e.g., for neurostimulation. In some embodiments, the therapeutic device 170 can deliver one or more drugs, for example, wherein the one or more drugs are enclosed in the therapeutic device 170. In some embodiments, the therapeutic device 170 can provide thermal stimulation. In some embodiments, the therapeutic device 170 can provide photostimulation (e.g., light based therapies). The therapeutic device 170 can adjust the application of the treatment or therapy as a function of the sensor data or sensed condition from the sensing device 110. For example, the therapeutic device 170 can increase or decrease the intensity of the electric pulses applied to the person or subject; the therapeutic device 170 can also prolong or shorten the duration of the electric pulses applied to the person or subject, as well as the overall length of treatment time.

In accordance with some embodiments, the sensing device 110 can communicate with one or more therapeutic devices 170 through an intermediate device such as the external hub 130 or an external controller.

The external hub 130 can be a smart phone or other computerized device that can communicate with the sensing device 110 using any wired or wireless communication band (e.g., Bluetooth, WiFi, infrared, ZigBee, WMTS, cellular data, and industrial, scientific, and medical (ISM) band communications). Without limitation, addition examples of the external hub 130 include a smart watch, a tablet, a personal digital assistant, or a computer. The sensor device 110 and the external hub 130 can use an industry standard communication protocol or a proprietary communication protocol. The external hub 130 can include a processor and associated memory that can receive the raw sensor data or the processed sensor data from the sensing device 110 and store it in memory for further processing or for communication to a remote system for further processing, such as the analytics system 140. The external hub 130 can include one or more sensors (e.g., accelerometer, GPS, temperature, light). The external hub 130 can include a network interface (e.g., wired such as Ethernet or wireless such as WiFi or 3G, 4G, 4G LTE mobile data) that enables the external hub 130 to communicate with other smart phones, computers, and systems, such as the analytics system 140 and other sources of data and information. In accordance with some embodiments of the invention, the external hub 130 and/or the analytics system 140 can further analyze the sensor data using analytics algorithms that either process the sensor data by itself or in combination with other available data. In accordance with some embodiments of the invention, the external hub 130 can analyze the sensor data and as a function of at least the sensor data, directly communicate with another device to control that device. For example, the external hub 130 can receive sensor data (either from the sensing device 110, its own internal sensor, or both) indicating the level of illumination in an environment, such as a room, and as a function of the sensed illumination data, directly turn on or off or dim one or more lights in the room.

In accordance with some embodiments of the invention, the external hub 130 can analyze the sensor data and as a function of at least the sensor data, indirectly communicate with another device through an interface, such as a separate control system 160 in order to control that device. For example, the external hub 130 can receive sensor data indicating the ambient temperature level in an environment, such as a room or the person or subject, and as a function of the sensed temperature data, directly control the heating and/or cooling (e.g., turn the HVAC system 150 on or off, or adjust the thermostat 160 set-point temperature up or down) for the room.

In accordance with some embodiments of the invention, the external hub 130 can send the raw sensor data or the processed sensor data (or both) to a remote analytics system 140 that can process and analyze the sensor data and the analytics system 140 can communicate directly or indirectly with other devices to control them and the environment.

In accordance with some embodiments of the invention, the external hub 130 together with remote analytics system 140 can process and/or analyze the raw or processed sensor data, optionally in combination with other data from other sensors or stored data, weather data, or date and time information, to determine one or more actions. The actions can include communicating with the target device 150 to control it directly or communicating with the remote controller 160 that controls the target device 150.

As shown in FIG. 1, in accordance with some embodiments, the analytics functionality can be distributed over one or more external hubs 130 in a network or cluster configuration to form a distributed processing system 120 to provide for distributed processing of the sensor and, optionally, other data. In accordance with some embodiments, the analytics functionality can be distributed over the external hub 130 and one or more computer systems or clusters (e.g., other external hubs 130, and/or analytics systems 140), in a distributed network or cluster system configuration 120 to provide for distributed processing of the sensor and, optionally, other data. Each of the computer systems that make up the cluster can communicate using wired cluster interconnect technologies and/or wireless communication technologies (e.g., Ethernet, WiFi, mobile data, such as, GSM, 3G, 4G, and 4G LTE) or other network communication technologies. The network can include networking equipment, such as, one or more wires, switches, hubs, wireless access points, and routers to enable communication between the devices and systems.

In accordance with some embodiments of the invention, the external hub 130 can be configured to communicate directly with one or more target devices 150 using wired or wireless communication (e.g., infrared, Ethernet, Bluetooth, WiFi, ZigBee, WMTS, cellular data, and industrial, scientific, and medical (ISM) band communications). In accordance with some embodiments of the invention, the external hub 130 can be configured to communicate directly with one or more controllers 160, using wired or wireless communication (e.g., infrared, Ethernet, Bluetooth, WiFi, ZigBee, WMTS, cellular data, and industrial, scientific, and medical (ISM) band communications). The controllers 160 can be controlled using an open or proprietary interface or an application programming interface (API) to control the target device 150.

The analytics system 140 can include one or more computers that are configured to receive the sensing data. The sensing data can be transmitted by the external hub 130 to the analytics system 140 over a public or private network. In accordance with some embodiments, the external hub 130 acts a gateway that forwards the sensor data to the analytics system 140 according to predefined instructions or configuration. The analytics system 140 can be, for example, a big data server (e.g., based on Hadoop, or another analytics engine) that can receive, store and analyze the sensor data according to a predefined analytical method or process. In accordance with some embodiments, as a result of the predefined analytical method or process, the analytics system 140 can generate one or more commands and/or data and send one or more of those commands and/or data to the external hub 130, the target device 150 or the controller 160. The commands can be used to control or change the operation of the external hub 130, the target device 150 or the controller 160.

In accordance with some embodiments, the smart phone 130 can send one or more commands (e.g., an instruction to perform some function or operation, or an acknowledgement that a function or operation has started or completed) and/or data (e.g., sensor data, user data, and environmental data) to the analytics system 140. The analytics system 140 can interpret and respond to the commands, for example, to retrieve data or process data or change the way the analytics system 140 processes the data. The response can include a command (e.g., an acknowledgement or instruction) and/or data (e.g., data or information requested, results of an analysis or other sensor data). The external hub 130 can use the data for further analysis by algorithms on the external hub 130 or to determine whether one or more commands and/or data should be sent to the target device 150 or the controller 160.

In accordance with some embodiments of the invention, the target device 150 can include a device that can communicate directly with the external hub 130. Thus, the target device 150 could be, for example, a light switch, an appliance (e.g., TV, refrigerator, dishwasher, or washing machine), a garage door opener, a door lock, a manned or unmanned motorized vehicle (e.g., car, truck, train, boat or airplane), a computer, a programmable controller, a sound system, an environmental control system (e.g., HVAC system, heating system, cooling system, humidifying system, dehumidifying system), a home automation system, and a communication system (e.g., voice/telephone, text messaging, email, facsimile, and chat). In accordance with some embodiments of the invention, the controller 160 can be, for example, a home automation controller (e.g., to control the target device 150, such as lights, HVAC, garage doors, door locks, appliances, and sound systems), an HVAC controller (e.g., thermostat), home entertainment system, a dispatch system (e.g., dispatching motorized vehicles, people and/or services), and a motor vehicle control system (e.g., controlling vehicle operation, including direction and navigation, safety, and vehicle environmental control).

Figure 2:
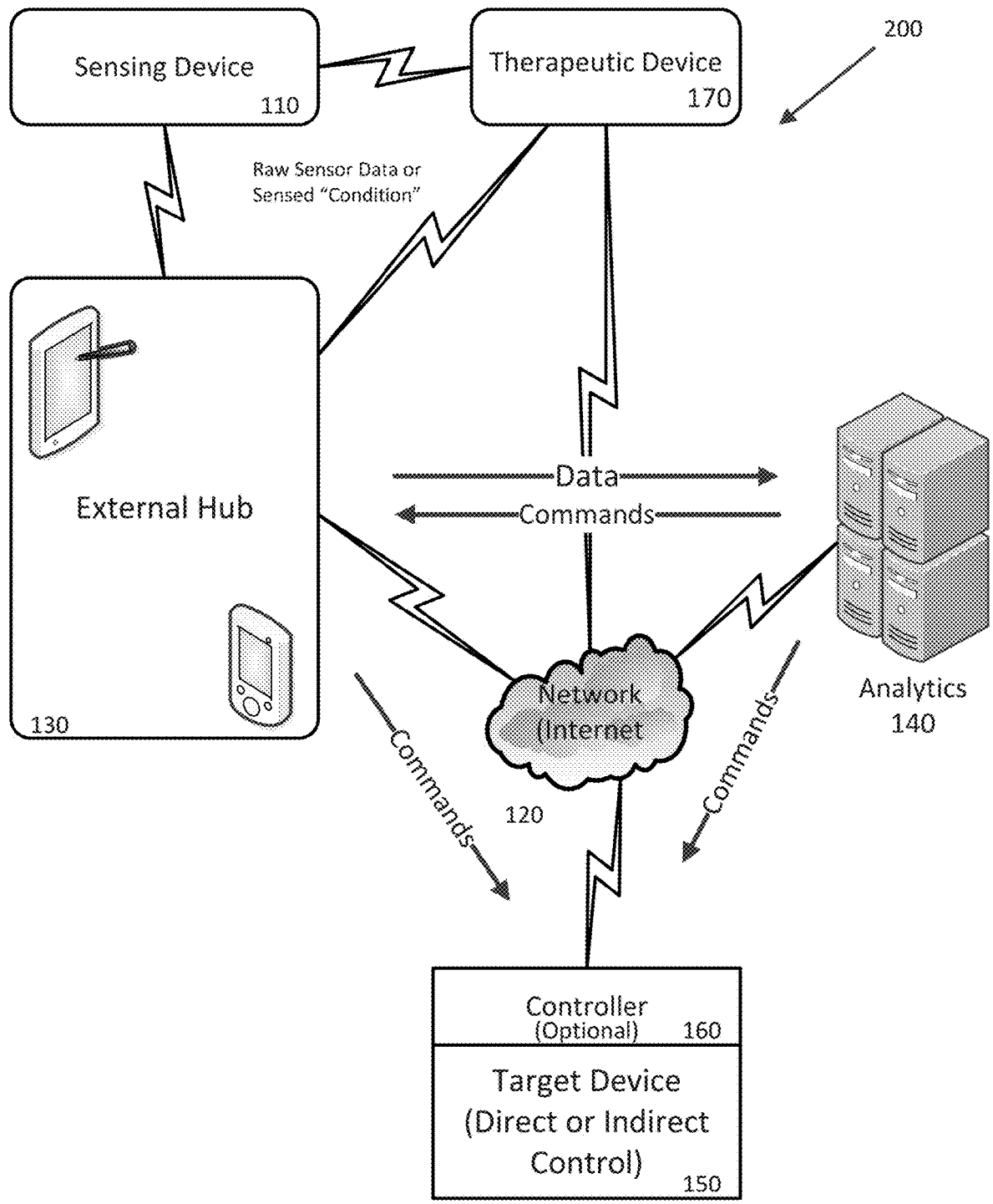
FIG. 2 is a block diagram of a system according to some embodiments of the invention.

FIG. 2 shows a system 200 according to some embodiments of the invention. In this embodiment, the system 200 can include one or more sensing devices 110, an external hub 130, one or more therapeutic devices 170, and optionally a target device 150 and/or controller 160. The therapeutic devices 170 can communicate directly over network 120 with other devices in the system. An optional analytics system 140 can also be connected to the system 200. The external hub 130 can be configured to communicate with the target device 150, the controller 160 and optional analytics system 140 over a common network 120, such as a LAN, or a WAN, such as the internet. The controller 160 can be connected to and used to control the target device 150, directly or indirectly. System 200 can include many of the same components as system 100 and operate similar to system 100.

While one sensing device 110 is shown as being connected directly to the external hub 130, in an alternative embodiment of the invention, one or more the sensing devices 110 (e.g., one or more worn by the person or subject and optionally, one or more not worn by the person or subject) could be connected to the external hub 130 through the common network 120. The external hub 130 can communicate with one or more sensing devices 110, one or more analytics systems 140, a target device 150 and a controller 160 over the common network 120. This enables external devices such as the analytics systems 140, and the external hub 130 to communicate directly with the therapeutic devices 170 to send commands and receive data directly from the therapeutic devices 170.

In operation according to some embodiments of the invention, sensor data from the sensing device 110 is received by the external hub 130. The sensor data can optionally be stored in memory. The sensor data can be sent to the network 120 to the analytics system 140 for subsequent processing. In accordance with some embodiments, the sensor data can be processed according to one or more algorithms or processes which determine whether one or more conditions relating to the sensor data meet one or more specified criteria. This can be accomplished by comparing one or more of the conditions to a predefined threshold and taking an action (or not taking an action) as a function of the comparison. For example, if a subject's body temperature (e.g., as a function of the sensor data from sensing device 110) is below a first predefined threshold and the environmental temperature (e.g., as function of data in the external hub 130 or controller 160) is below a second predefined threshold, then the system 100 or 200 can increase the environmental temperature by a first incremental amount by sending a command to the thermostat or the home automation controller (e.g., controller 160) to cause the heating system to turn on and raise the environmental temperature by a predefined amount or cause the air conditioning system to turn off, to allow the environment to warm up. If the subject's body temperature does not increase after the environmental temperature is increased by the first predefined amount, the system could send a second command to the thermostat or the home automation controller to cause the heating system to turn on (if necessary) and raise the environmental temperature by a second predefined amount (which could the same as the first) or cause the air conditioning system to turn off or stay off, to allow the environment to warm up. After the passage of a set period of time or number of heating cycles, if the subject's body temperature does not rise, the system could send an alert message to a family message or care provider.

In accordance with some embodiments, the sensor data can be processed according to one or more algorithms or processes which determine whether one or more conditions relating to the sensor data meet one or more specified criteria (e.g., threshold values) or are likely to meet one or more specified criteria in the future. This can be accomplished by extrapolating existing data or analyzing trends in the data, to determine a predicted value for one or more conditions in the future and comparing the predicted value to a predefined threshold. For example, if a subject's body temperature is dropping as demonstrated by a recorded drop in temperature over time, based on the determined rate of change, the algorithm can determine the warning time, e.g., the amount of time it will take for the subject's body temperature to drop below a predefined threshold under the current environmental conditions (e.g., the current ambient temperature). Using other information, such as the heating efficiency of the heating system or warming rate (e.g., when the air conditioning is turned off), the algorithm can determine a warm-up time, e.g., how long it will take the heating system to warm up (e.g., raise the temperature of) the environment by a first amount. If the warning time is greater than the warm-up time, the system 100, 200 can wait some time less than the difference between the warning time and warm-up time and check the subject's body temperature. Alternatively, the system 100, 200 can begin to raise the heat (or keep the air conditioning off), and monitor for any changes in the subject's body temperature and increase or decrease the environmental temperature depending upon whether the subject's body temperature continues to drop or whether it begins rise.

Figure 3:
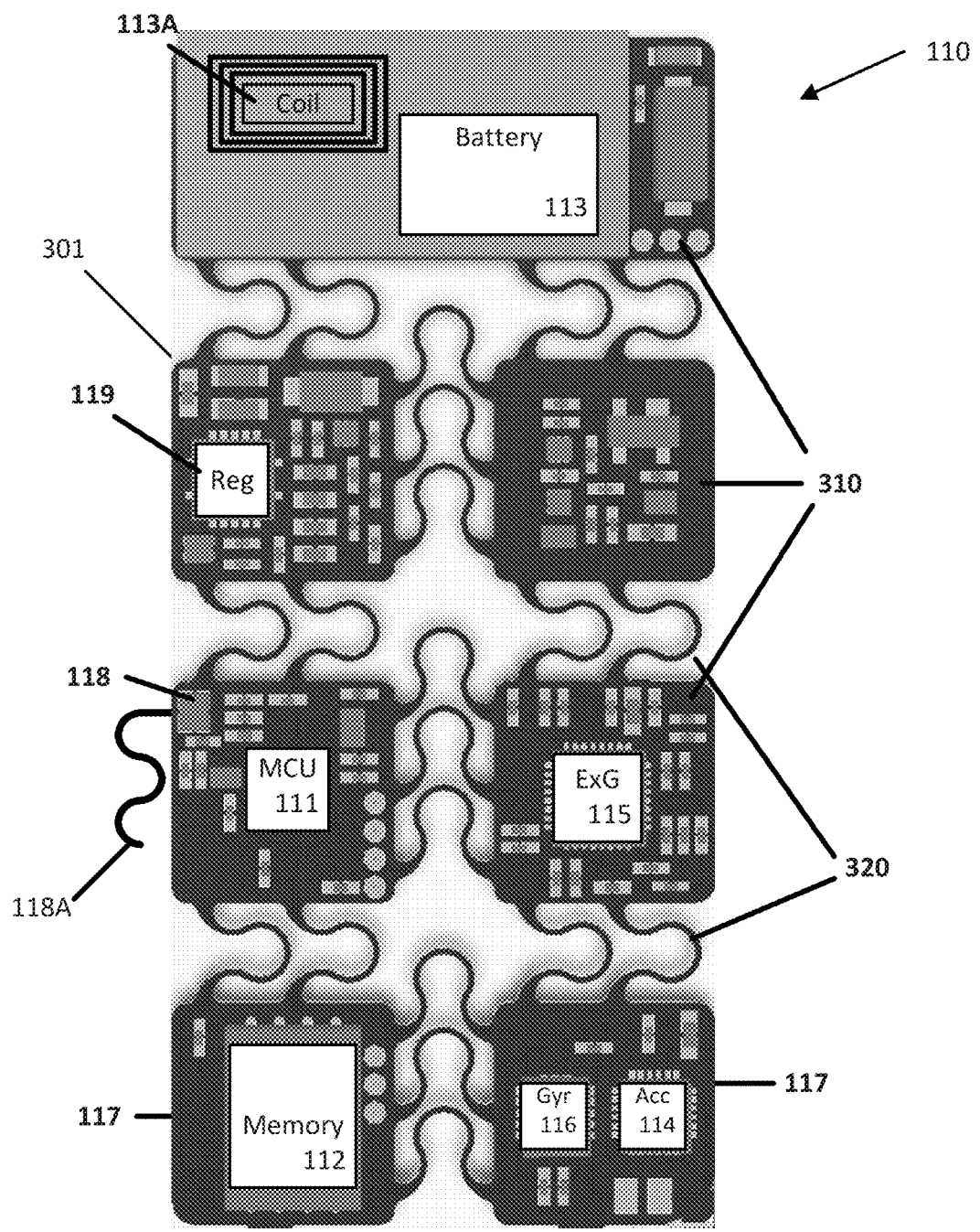
FIG. 3 is a block diagram of a sensing device according to some embodiments of the invention.

FIG. 3 shows one embodiment of a sensing device 110 according to the invention. In accordance with some embodiments of the invention, the sensing device 110 can include a plurality of components mounted on device islands 310, wherein each device island 310 can be connected to an adjacent device island 310 by a flexible interconnect 320, enabling the sensing device 110 to flex and stretch and conform to irregular surfaces, such as those of the body of a person or subject. The sensing device 110 can be encapsulated in a flexible or stretchable material, such as, silicone or PDMS. The sensing device 110 can include an adhesive material that enables the sensing device to adhere to the skin of a person or subject or the surface of an object. The sensing device 110 can optionally include one or more user interface components, such as buttons, lights (e.g., LEDs), displays, speakers or vibrators that enable a user or person to interact with the device using visual, audible and sensory cues. These user interface components can be used to provide operational, configuration, and biometric performance feedback to a user directly, such as, through visual and tactile output capabilities via LEDs and vibration motors.

The sensing device 110 can include a processor 111 and associated memory 112 and a battery 113 which serves as a power source. An induction coil 113A can be used to charge the battery 113. The sensing device 110 can include one or more sensors, including an accelerometer 114, an ExG (e.g., EKG, ECG, EMG, or EEG) sensor 115, a gyroscope 116, and one or more electrodes 117 (on the back side of the device shown in FIG. 3). The sensing device 110 can also include wireless transceiver 118 (e.g., such as Bluetooth™, WiFi, mobile data) and an antenna 118A to enable the sensing device 110 to communicate with external hub 130 and therapeutic device 170.

In accordance with some embodiments, the memory 112 can store one or more computer programs, including an operating system (e.g., Linux) as well as one or more application programs, functions and processes that can be used to control the operation of the sensing device 110. One or more programs, functions or processes can be used to collect accelerometer and/or gyroscope data, which includes motion and acceleration information in 1, 2 or 3 dimensions as well as temperature data. One or more programs, functions or processes can be used to collect bio-potentials in the form of ExG data from the ExG sensor. The ExG data can include data representative of at least one of the following bio-potential signals: electrocardiogram (e.g., EKG or ECG) signals, electromyogram (e.g., EMG) signals or Electroencephalogram signals (e.g., EEG), depending on how the one or more programs, functions or processes configures the ExG sensor 115. The sensing device 110 can include one or more electrodes 117 that can be placed in contact with the skin to receive these signals. In accordance with some embodiments of the invention, the EKG data can be used to determine heart rate and heart rate variability as well as recovery rate and the EMG data can be used to determine muscle activation.

In operation, the sensing device 110 can be configured using one or more programs, functions or processes to collect raw sensor data and store the data in memory 112. In accordance with some embodiments, one or more programs, functions or processes running on the processor 111 can process and/or analyze the raw sensor data and generate processed sensor data, for example, by filtering the raw data to remove noise and/or artifacts and/or to normalize the raw sensor data. In accordance with some embodiments, the raw sensor data and/or the processed sensor data can be further processed by computing descriptive analytics (e.g., minimum values, maximum values, mean values, median values, mode values, standard deviation and variance values, and higher moments such as kurtosis) on one or more sets of samples of the data, and comparing such values against the comparable values of a larger cohort of relevant individuals, or against prior measurements collected on the same individual. In accordance with some embodiments, the raw sensor data or the processed sensor data can be further processed to extract specific features or characteristics of the signal like the dominant frequency, range, root mean square value, correlation coefficient, heart rate, respiration rate, cadence etc. The features can be further processed using one or more algorithms (e.g. decision tree, state machine, and/or linear/logistic regression) to detect or predict events (e.g. activity types, falls, stumbles, seizures, tremors) or to detect or predict status (e.g., state of mind, mental condition and/or attitude). In accordance with some embodiments, the raw sensor data can be converted to tokens or symbols representative of two or more raw sensor data values (e.g. sensed conditions). The raw sensor data can be processed in real time as it is received from the sensor element or it can be processed in blocks after a predefined number of raw sensor data values are received. The raw data and the processed data can be stored in memory 112, until it is transmitted to a remote device.

The sensing device 110 can process the data to generate one or more higher order biometrics, by processing the raw data to determine, for example, activity type detection, activity-specific or body location-specific performance indicators, gesture recognition, posture quality, and sleep quality. The sensing device 110 can receive and process external commands which cause the device to modify its configuration and/or operation for collection, processing, and reporting of sensor data, including turning on or off various sensor combinations, changing sampling rates and measurement ranges, modifying buffering and filtering schemes, and applying different digital signal processing and algorithms to raw sensor output to produce different streams of data and/or different sets of higher order biometrics around activity tracking, activity performance, and activity quality data. Based on the biometrics determined and/or other data, the sensing device 110 can, based on an algorithm or set of rules, select a sensing modality which is optimal for a particular activity or on-body location that has been detected, and automatically modify its configuration and/or operation for collection, processing, and reporting of sensor data, including turning on or off various sensor combinations, changing sampling rates and measurement ranges, modifying buffering and filtering schemes, and applying different digital signal processing and algorithms to raw sensor output to produce different streams of data and/or different sets of higher order biometrics around activity tracking, activity performance, and activity quality data.

In accordance to some embodiments of the invention, when the sensing device 110 is connected using, for example, the wireless transceiver 118 (e.g., Bluetooth™, WiFi or Zigbee) to the external hub 130 or therapeutic device 170, the raw sensor data and/or the processed sensor data can be transmitted using the wireless transceiver 118 to the external hub 130 or therapeutic device 170 and stored in the memory of the external hub 130 or therapeutic device 170. In accordance with some embodiments of the invention, the sensor data can be transmitted by the external hub 130 or device 170 to the analytics system 140 for long-term storage and further analysis.

The systems 100, 200 can be configured to enable many different data flows. In accordance with some embodiments of the invention, the raw data or processed sensor data and metrics can flow from the sensing device 110, through the external hub 130 or therapeutic device 170, to the analytics system 140 or a data storage system associated with the analytics system 140. The sensor data (e.g., raw or processed) can be pre-filtered, conditioned, manipulated, or combined with other data within the external hub 130. The sensor data (e.g., raw or processed) can also be filtered, conditioned, manipulated, or combined with other data within the data storage and analytics system 140, and can be used to tune the electrical/sound/light/neuromodulation and/or drug therapy delivered by the therapeutic device 170 (e.g., a nerve stimulation device or drug-delivery system).

In accordance with some embodiments of the invention, processed sensor data or other data can flow from the data storage and analytics system 140 through the external hub 130 or therapeutic device 170 and back to the sensing device 110. Processed data (e.g., commands, control instructions, or higher order information, such as, software and algorithms for system upgrades and updates) can flow from the data storage and analytics system 140 to the external hub 130 or therapeutic device 170, and through the external hub 130 or therapeutic device 170 to the sensing device 110. The data can be filtered, interpreted, validated, and/or combined with other data within the smart device. The data can also be filtered, interpreted, validated, and/or combined with other data within the sensing device 110.

In accordance with some embodiments of the invention, the raw data or processed sensor data (metrics) can flow from the sensing device 110 (optionally through the external hub 130), through the data storage and analytics system 140 to one or more external systems, such as, machines, equipment, implantable devices and environmental control systems. Processed data (commands, control instructions, or higher order information, such as, software and algorithms for system upgrades and updates) can flow from the data storage and analytics system 140 to external machines or equipment (e.g., exercise equipment, power tools, motorized vehicles) and/or environmental control systems (such as ambient temperature control system, lighting, or alerting and alarm systems). The data can be filtered, interpreted, validated, and/or combined with other data within the external machine, equipment or environmental control system. The data can also be filtered, interpreted, validated, and/or combined with other data within the sensing device 110.

In accordance with some embodiments of the invention, body worn conformable sensors, such as sensing device 110 can be used to quantitatively or qualitatively measure a variety of different health parameters from the human body. The sensing device 110 can be attached to any location of the body of a person or subject, including but not limited to, forehead, temple, neck, shoulder, chest, upper arm, forearm, wrist, hand, abdomen, waist, shin, ankle, hip, thigh, and foot. Depending on the location of the body and the sensors included in the sensing device 110, the specific physiologic and biologic parameter measured by the sensing device 110 can differ (see Table 1). It should be noted that a sensing device 110 at a single location can measure one or more physiologic and biologic parameters.

Figure 5:
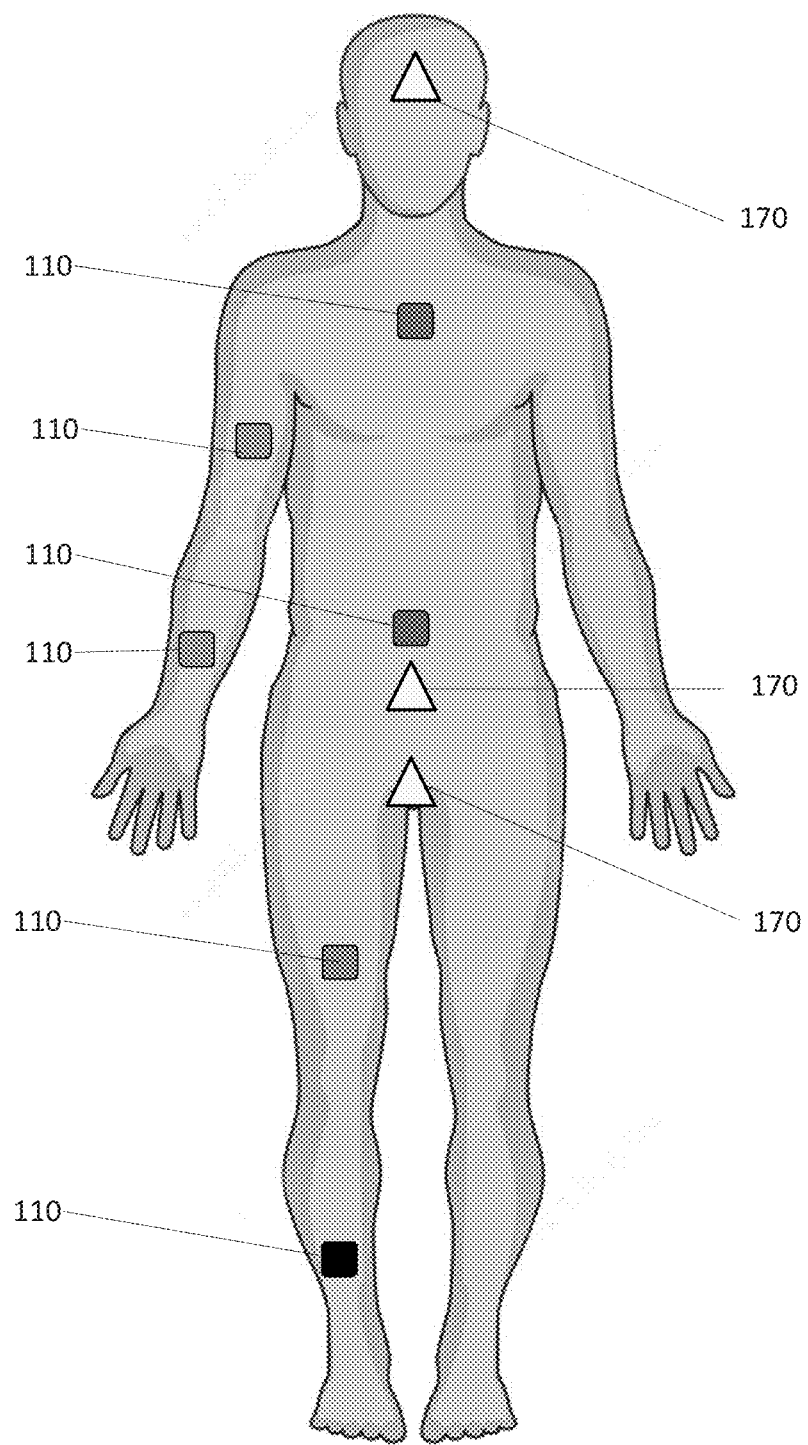
FIG. 5 shows a diagram showing examples of sensing device locations and therapeutic device locations according to some embodiments of the invention.

FIG. 5 shows a diagram of examples of sensing device 110 placement locations and therapeutic device 170 placement locations according to some embodiments of the invention. The therapeutic device 170 can be placed on or implanted in any location of the body, for example to provide optimum application of therapy, for example, the vagus nerve, the phrenic nerve, the hypoglossal nerve, any of the peripheral nerves, the brain (e.g., deep brain stimulation), the spinal cord, the dorsal ramus nerve, the dorsal root ganglion, baroceptors (e.g., carotid, arterial, cardiopulmonary), and any of the body's organs (e.g., bladder, spleen, liver, kidneys, prostate, gall bladder, colon and lacrimal gland). Table 1 shows exemplary physiologic and biologic parameters measured as a function of the location of the sensing device 110

TABLE 1

| Location of the sensing device 110 | Physiologic and biologic parameters measured |
| --- | --- |
| forehead | body temperature, core temperature, EEG signals |
| temple | heart rate, heart rate variability |
| neck | body temperature, core temperature, heart rate, heart rate variability |
| shoulder | EMG, temperature, acceleration, range of motion |
| chest | heart rate, heart rate variability, ECG signals, EMG signals, respiration rate, respiration rate variability, acceleration, coughs |
| upper arm | EMG, acceleration, gyration, range of motion |
| forearm | EMG signals, acceleration, gyration, daily activities, range of motion, motion |
| wrist | daily activities, range of motion, motion |
| hand | daily activities, range of motion, motion |
| abdomen | EMG signals, acceleration |
| waist | Acceleration, gyration |
| shin | EMG signals, acceleration, gyration |
| ankle | EMG signals, acceleration, gyration |
| hip | Acceleration, gyration |
| thigh | daily activities, , range of motion, motion, stride length |
| foot | daily activities, range of motion, motion, stride length |

The physiologic and biologic parameters that can be measured by the sensing device 110 can include bio-potentials, such as, ECG, EMG, EEG and respiration as well as acceleration and angular velocities related to motion. The ECG signals can be used to determine heart rate, heart rate variability and recovery rate. In addition ECG signals can be used to determine abnormalities associated with heart function (e.g. seizures and/or arrhythmias including tachycardias, bradycardias, atrial fibrillation, atrial flutter, and/or supraventricular tachycardias. The EMG signals can be used to determine muscle activation (e.g., contractions, spasms, tremor, rigidity, myopathy, and/or muscular dystrophy). The EEG signals can be used to measure brain activity and determine mood and attitude. The raw accelerometer signals can be transformed into signal parameters or features such as frequency content in specific frequency bands, acceleration vector amplitudes, acceleration vector direction changes as a function of time, etc. and these features can be correlated with relevant metrics such as heart rate, respiration rate, as well as motion related to walking, running, physical activity, posture, tremors, coughs, snoring, frailty, and falls. The accelerometer signals can also be used to detect and/or measure, for example, seizures, gait and balance problems, steps and/or cadence, energy expenditure (together with heart rate and/or respiration rate), range of motion, and other activity types (e.g., swimming, cycling, rowing, throwing, swinging, kicking, punching, etc.)

These parameters can be used for detection or prediction of medical conditions and/or as an indicator of general health and well-being of an individual. In accordance with some embodiments of the invention, a system that includes a wearable body sensor can be connected to an information gateway (e.g., the external hub 130) to control a set of external devices nearby the user. The system can act in a coordinated manner to provide responsive action for influencing the wellbeing of an individual. For example, implantable neuromodulation devices 170 can be configured and controlled for delivering therapy according to the signals captured by the wearable body sensor 110.

In accordance with some embodiments of the invention, accelerometer data captured by a conformable sensing device 110 affixed to the chest can be used to detect and record multiple physiologic signals including heart rate, respiration, coughing at rest, by detecting the mechanical vibrations resulting from the motions of the chest cavity and rhythmic movements of the heart (heart rate) sensed on the chest wall. FIG. 5 shows a comparison of raw accelerometer data (top), and filtered accelerometer data (middle and bottom) that maps directly to breathing frequency and amplitude. FIG. 6 shows an exploded view of raw accelerometer data (top) showing the high frequency heart beat bursts riding on the low frequency breathing pattern envelope and filtered accelerometer data (middle and bottom) showing low-frequency patterns of oscillation, which map to breathing patterns.

In accordance with some embodiments of the invention, heart beat information can be derived from the high frequency portion of the accelerometer signal, and respiration information can be derived from the low frequency portion of the accelerometer signal. For example, to derive heart rate information, the raw accelerometer data can be filtered through a band pass filter with a high pass cutoff frequency of 2 Hz and low pass cutoff frequency of 45 Hz. Next, the resultant of the X, Y and Z axes is determined by taking the square root of the sum of square of each axis. To amplify the high frequency components, the signal is then differentiated. The differentiated signal is then processed by a state machine with an adaptive threshold to detect the heart beats and calculate the heart rate using a Pan-Tompkins or similar algorithm. See, Pan, Jiapu; Tompkins, Willis J., "A Real-Time QRS Detection Algorithm," *Biomedical Engineering, IEEE Transactions on*, vol. BME-32, no. 3, pp. 230, 236, March 1985, which is hereby incorporated by reference.

For example, to derive the respiration rate information, the raw accelerometer signal can be filtered using a low pass filter having a cutoff frequency of 2 Hz. The respiration rate can be estimated based on the method described in the following publication: A. Bates, M. J. Ling, J. Mann and D. K. Arvind "Respiratory Rate and Flow Waveform Estimation from Tri-axial Accelerometer Data", Proc. Int. Conf. on Wearable and Implantable Body Sensor Networks, pages 144-150, Singapore, June 2010.

The flexible or stretchable sensing device 110 according to the invention can be used for sleep quality analysis and treatment. Sleep quality analysis (e.g., sleep studies) typically require multiple biometric data streams to determine sleep states including awake state, light sleep, deep sleep and rem sleep. In the prior art, these sleep studies tend to collect multiple streams of data from patients, including respiration rate/patterns, heart rate/heart variability, roll over frequency, motion, EEG, and other parameters using wired sensors to evaluate sleep quality. In accordance with some embodiments of the invention, one or more flexible or stretchable conformable sensing device 110 according to the invention can be used to monitor multiple sleep parameters—respiration, heart rate, roll-over frequency and temperature—with an accelerometer sensor housed in an extremely soft and stretchable package that is sufficiently sensitive to sense very small mechanical perturbations caused by breathing and heart beats. In accordance with some embodiments of the invention, a single conformable sensing device 110 can be adhered to the chest to detect respiration, heart rate, roll-over frequency and temperature using just an accelerometer sensor. The sensor data can be transmitted wirelessly to the smart phone or communications hub 103 that stores the accelerometer sensor data and can forward the sensor data to a remote computer system for subsequent analysis. In accordance with some embodiments of the invention, two or more conformable sensing devices 110 can be used. A first conformable sensing device 110 can be adhered to the chest to detect respiration, heart rate, roll-over frequency and temperature using just an accelerometer sensor and a second conformable sensing device 110 can be adhered to the head and using the ExG sensor detect EEG data in addition to the accelerometer data collected by the first conformable sensing device 110.

The accelerometer data and optionally, the EEG data can be processed and analyzed by the external hub 130 and/or analytics system 140 to determine the sleep state of the person or subject. In one embodiment, the therapeutic device 170 could be an implanted electric stimulator device to treat over-active bladder syndrome. The wearable sensor data can measure sleep quality and deliver feedback to the therapeutic device 170 to correct the over-active bladder syndrome. This information can be used to control therapeutic device 170 or external environmental factors in the room where the person or subject is sleeping to improve sleep quality. These environmental factors include the ambient temperature, humidity, noise (e.g., music and environmental noise), and light (e.g., light frequency and amplitude) in the room.

In accordance with some embodiments of the invention, the system can monitor one or more therapeutic devices 170 or external environmental factors, including ambient temperature, humidity, noise (e.g., music and environmental noise), light (e.g., light frequency and amplitude) in the room and bed firmness, while recording the accelerometer and optionally, EEG data. The accelerometer data and optionally, the EEG data, can be used to detect and identify the sleep states experienced by the person or subject during the night. The system can change one or more environmental factors and observe how it effects the duration of the various sleep states. For example, during deep sleep or rem, the external hub 130 can increase or decrease the ambient temperature and/or bed firmness and observe whether the change in these environmental parameters causes an increase in the duration of deep sleep or rem sleep. In another example, the external hub 130 can use the accelerometer data and optionally, the EEG data to strategically select background sounds and/or music to be played during high quality sleep states to induce a deep sleep and/or rem sleep as well as induce longer durations of these sleep states. In accordance with some embodiments, music transitions (e.g., changes in genre/beat/amplitude) can be selected to transition a subject out of deep sleep in time for a pre-scheduled wake up time.

In accordance with some embodiments, the system 100 can (a) establish a correlation between parameters descriptive of music and/or sound (e.g., styles, rhythm genre and/or frequency content, etc.) and parameters indicative of deep sleep (e.g., low heart rate and respiration rate, lower core body temperature, less movement, etc.) across a sample or larger group of users, (b) establish a correlation between parameters descriptive of music and/or sound ((e.g., styles, rhythm genre and/or frequency content, etc.) and parameters indicative of light sleep (e.g., faster heart rate and respiration rate, higher core body temperature, more movement, etc.) across a sample or larger group of users, and (c) controlling the sound environment (e.g., the selected styles, rhythm genre and/or frequency content of sound) accordingly to facilitate or induce a sleep state (e.g., go-to-sleep, enter deep sleep, enter lighter sleep, and/or wake-up) as desired based on the goals of a particular subject.

Music and sound can be used to affect the mental state (e.g. increase or decrease arousal) of a person or subject, and thereby influence the physiology (e.g. increased or decreased HR, galvanic skin response or respiration rate). For example, if an individual is trying to meditate, the wearable sensor can monitor the heart rate, respiration and galvanic skin response to determine the mental state (e.g. relaxed or agitated, and trends or changes in state) and select a song/music which has a calming effect. In accordance with some embodiments, if the determined physiological response (e.g., as measured by the heart rate, respiration rate and galvanic skin response) indicates that the selected song is having (or has had in the past) the desired effect, the song/music/sound would continue playing and any subsequent song/music/sound would be selected to have similar characteristics. On the other hand, if the desired response is not achieved, the system would select a different genre/type of song/music/sound. Over time, the algorithm can learn to select the song/music/sound or type of song/music/sound that is more likely to help the individual meditate and thus become more personalized.

In accordance with some embodiments of the invention, the system can use a flexible or stretchable conformable sensing device 110 in a system for detecting respiratory paralysis of the expiratory muscles that can accompany Asthma or COPD or Sleep Apnea events and pneumonia. The sensing device 110 can use the accelerometer to monitor respiration function to detect respiration rate, respiration rate variability, depth of breaths, respiration as a function of body position, and/or various kinds of respiratory patterns indicative of problems such as asthma, snoring, sleep apnea, etc. which may have an adverse effect in quality of life, quality of sleep, etc. and statistics derived from the same (e.g. short and long term fluctuations, variance). If respiratory paralysis or signs of impending respiratory paralysis are detected, the external hub 130 can cause a change in the environment, such as increasing the levels of oxygen and/or nitrogen in the room, causing the external hub 130 to record the event on a video camera or present a program or application to the person that trains the person to breath rhythmically or causes the person to breath rhythmically (e.g., using music or other organized sounds such as simple tones or beats). In accordance with some embodiments, abnormal breathing patterns can be detected by comparing (and testing for deviations of) real time measurements of sleep-relevant metrics (e.g., heart rate, respiration, motion and temperature based measures) against a normal baseline for a particular subject or a sample or larger group of similar subjects, as well as by comparing such real time measurements against a library of data sets known to contain patterns and metrics indicative of certain abnormalities.

In accordance with some embodiments of the invention, the system can be used to evaluate electrical stimulation of the spine as a method to improve clinical signs and symptoms of heart failure. The therapeutic device 170 can be an implantable pulse generator (IPG) or neurostimulator, similar to a cardiac pacemaker. With a lead or wire, the therapeutic device 170 can be connected to the spinal cord to deliver low-intensity electrical pulses. The one or more sensing devices 110 can be used to monitor heart-relevant metrics (e.g., hear rate, heart rate variability, respiration rate, respiration rate variability, muscle potentials, motion, stride length, fluid retention in the limbs and chest). The efficacy of the electrical stimulation method can then be determined by comparing the data obtained from the one or more sensing devices 110 against a normal baseline. The sensor data from the one or more sensing devices 110 can also prompt the therapeutic device 170 to change the intensity and/or duration of the electrical pulses. The effect of such a change in intensity and/or duration of the electrical pulses can be assessed by using the data obtained by the one or more sensing devices 110.

In accordance with some embodiments of the invention, the system can be used to automatically modify the environment of Multiple Sclerosis (MS) patients when they experience a temporary worsening of symptoms due to, for example, an increase in core body temperature. The system according to the invention can include a sensing device 110 that can detect core body temperature as well as worsening of MS related symptoms like gait and balance. The accelerometer data can be used to detect a rise in core body temperature and an associated adverse change in gait and/or balance. In accordance with some embodiments of the invention, adverse changes in gait can be detected and measured by measuring temporal (e.g. stride time, stride time variability, peak angular velocity during swing, double support time) and spatial (e.g. stride length, smoothness of flight path, asymmetry, ground clearance) parameters associated during ambulation. Adverse changes in balance can be detected by measuring transition time (e.g. sit-to stand, lying-to-sitting), sway area of the center of mass while standing, frequency of stumbles/falls and posture.

In accordance with some embodiments of the invention, the system can be used to monitor core body temperature, gait and balance to identify one or more relationships between changes in body temperature and a worsening of MS related symptoms like gait and balance. The sensed body temperature, gait and balance can be used to determine when to send a signal to the thermostat to automatically adjust the ambient temperature or lighting in the room, as a way to automatically improve the wellbeing of a patient. For example, in diseases like Multiple Sclerosis, there is a strong causal relationship between core body temperature and temporary worsening of disease symptoms. In accordance with some embodiments of the invention, the sensor device can use the accelerometer data to detect a change (e.g., deterioration or variation) in the measures associated with gait and/or balance and use the temperature sensor to detect and measure an increase in body temperature and be programmed to respond to changes in these conditions by sending a signal to the thermostat to reduce the ambient temperature. Over time, the system would learn this relationship for individual user to optimize this response to prevent/minimize future adverse events.

In accordance with some embodiments of the invention, the system can be used to monitor epilepsy and stroke patients to detect seizure events that occur in the nighttime. These nocturnal seizures are often difficult to diagnose and characterize as they are not directly witnessed by a caregiver or clinician. The system can monitor parameters including HR, respiration rate and motion to build mathematical models or profiles that indicate the onset of such seizures. In accordance with some embodiments of the invention, the system can detect a nocturnal seizure from accelerometer data and cause a predefined action to occur such as sending an alert (e.g., an audible alarm, a text message or phone message) to a family member or care giver, initiating a video recording device to capture the event for retrospective medical decision-making or controlling the lighting system to ease the effects of seizure.

In accordance with some embodiments of the invention, the system can be used to assist patients with Parkinson's Disease (PD), multiple sclerosis (MS), Huntington's disease, essential tremor, depression, ADHD, and OCD who may experience difficulty performing common activities of daily living due to their motor symptoms like tremor, bradykinesia (slowness) and dyskinesia (involuntary jerking). Such activities include eating, using a computer (mouse/keyboard) and driving. In accordance with some embodiments of the invention, the system can be used to monitor and measure one or more characteristics (e.g., frequency, amplitude etc.) of the motion due to the PD or MS symptoms and communicate with external systems and devices to introduce changes in their environment. For example, where the system determines that the person is experiencing tremors or jerking of their hands, while driving a motor vehicle, the system can communicate with a controller in the vehicle or the steering system directly to cause damping of the steering wheel. Severe tremors can interfere with the ability of an individual with Parkinson's disease to drive because of the excessive shaking makes it hard to use the steering wheel to control the car. The frequency associated with tremor in patients with Parkinson's disease is typically between 3-8 Hz. In accordance with some embodiments of the invention, a sensing device 110 placed on the affected arm or hand of a person or subject can be used to detect the presence or absence and severity of tremor at any given time. Based on the tremor profile, the steering wheel controller in the car can be controlled by the sensing device 110 or the external hub 130 to adjust itself to reject steering wheel movements in the tremor frequency band.

Another such example is that of a patient with tremor using a computer mouse. Shaking associated with tremor can make it difficult for an individual to use a mouse to operate a computer. In accordance with the invention, a software filter in the computer can be tuned to the frequency of the tremor motion and controlled by the sensing device 110 (or the external hub 130) to reject high frequency movements; thus making the mouse easier to use.

In certain patient population (e.g. Parkinson's disease), rhythmic cueing and music or sound can have an immediate impact on the physical status of the person or subject. For example, patients with Parkinson's disease often experience gait disturbances (e.g. freezing of gait) where it becomes difficult for an individual to initiate gait or walk with a regular gait profile. Rhythmic beats and certain music or sound patterns have shown to influence gait in patients with PD. A wearable sensing device 110 can be used to detect gait abnormalities in a patient and automatically send a message to the external hub 130 to play a rhythmic pattern that could alleviate the problem and help the individual improve their gait. See, for example, McIntosh G C, Brown S H, Rice R R, Thaut M H. Rhythmic auditory-motor facilitation of gait patterns in patients with Parkinson's disease. Journal of Neurology, Neurosurgery, and Psychiatry 1997; 62(1):22-26, which is hereby incorporated by reference.

Rhythmic music or sound and temperature have been shown to help promote relaxation and sleep among patients who would otherwise be wakened by involuntary movements. Music therapists have reported various rhythms or musical styles that can help with walking, balance, and movement in PD and MS patients. Control of this music in the environment through direct wireless connection to a wearable device that monitors symptoms, can thus serve as an automated way to control the symptoms of Parkinson's disease.

In accordance with some embodiments of the invention, the system can be used to control actuated prosthetic devices. For example, the sensing device 110 can detect EMG signals adjacent to an amputated limb and use that signal to control actuators in the prosthesis. EMG activation patterns can be detected from muscles adjacent to the amputated limb and used to measure and/or determining intent or characterize fatigue/cramping to improve the control of the prosthetic device. In addition, other sensing devices 110 can be used to sense physical parameters from one or more locations on the body to detect, for example, center of mass motion from the waist/chest or arm swing from the wrist or heart rate) and control or adjust the actuators (e.g., softer or harder force, or more support or less support) in the prosthetic device to respond adaptively in order to improve the operation and performance of the prosthetic device.

In accordance with some embodiments of the invention, the sensing devices 100 can be applied to the body in locations away from the amputation site to detect patterns in the motion and physiological signals that could be used to control the functioning of a prosthetic device. For example, accelerometer data can be used to tracking the center of mass motion of a person or subject to detect or measure the person or subject's balance (e.g., balance, unbalanced, or falling) and send signals to the prosthesis to control the prosthetic device to improve balance. In accordance with some embodiments of the invention, the sensing device 110 can also monitor the heart rate. respiration rate and motion of an individual to determine and measure energy expenditure and fatigue level of the person or subject to control the prosthetic device to increase or decrease the power output. For example, if the heart rate and respiration rate are elevated (perhaps because of steep terrain, which can be detected using the GPS on the external hub 130), the sensing device 110 or external hub 130 could control the prosthetic device to increase the power output to make it easier for the individual to walk.

In accordance with some embodiments of the invention, the sensing device 110 can be worn on the body and used to monitor heart function and respiration function (sensor data) while the person or subject is exercising on an exercise machine (e.g., a treadmill, an elliptical machine, a stair climbing machine or a rowing machine). During the exercise period, the sensor data can be used to determine a level of stress as a function of one or more of these parameters (e.g., heart rate, heart rate variability, recovery rate, and respiration rate) and the level of stress can be used to change the operation (e.g., speed, slope, and/or resistance) of the exercise machine to provide for optimum training.

In accordance with some embodiments of the invention, the sensor data can be transmitted to the exercise machine wherein a data processing system connected to the exercise machine similar to the external hub 130 processes the sensor data to determine a level of stress and a desirable level of speed, slope, and/or resistance for the person on the exercise machine for optimal training. The data processing system in the exercise machine can change the speed, slope, and/or resistance dynamically as function of the determined level of stress to provide for optimal training. In accordance with some embodiments, the sensor data can be sent to an external hub 130 that processes the sensor data and determines the optimal training speed, slope, and resistance for the person. The external hub 130 can communicate with exercise machine to change the speed, slope, and/or resistance of the machine. For health and safety purposes, where the sensor data indicates that a dangerous health condition exists, the system receiving the sensor data (e.g., the data processing system in the exercise machine or the external hub 130) can cause the exercise machine to stop to prevent injury to the person using it.

Over time, the data processing system or the external hub 130 can modify the selected training speed, slope, or resistance as function of past workouts. For example, where the person was able to sustain a predefined level (e.g., speed, slope, and/or resistance) for a specific duration of time in the past, the system can increase the speed, slope, resistance and/or duration to enhance training. Further, using a combination of the past workout profiles and physiological responses like heart rate, heart rate variability and heart rate recovery in the context of exercise intensity level, the system can determine or measure an indication of whether the person or subject is over training (e.g., and recommend a reduction or change in exercise level or intensity) or under training (e.g., and recommend an increase or change in exercise level or intensity).

In accordance with some embodiments of the invention, the system can be used to monitor the operators of motor vehicles including automobiles, trains, boats and airplanes. For example, where the sensor data indicates that the person is entering into or is in a disabled condition (e.g., a stroke or heart attack), the external hub 130 or the vehicle control system can cause the vehicle to stop moving and/or alert another operator or a central station of the condition. In this embodiment, the external hub 130 can communicate with vehicle control system to disable or slow the engine, apply the brakes or other remedial action to avoid injury when the operator becomes disabled. Alternatively, the vehicle can include a controller or system that receives the sensor data directly and automatically initiates a control process that disables or slows the engine, applies the brakes or initiates other remedial action to avoid injury when the operator becomes disabled. Similarly, where the sensor data indicates that the person (e.g., the operator) is intoxicated or impaired, for example based on erratic or unstable movements, the vehicle can be prevented from starting or otherwise put into gear. Alternatively, where the sensor data indicates that the person (e.g., the operator) is sleepy or slow to react, the system can activate control systems to turn on or change environmental controls to change the motor vehicle cabin temperature or environmental sounds (e.g., music) to stimulate the operator and change their state.

In accordance with some embodiments of the invention, the system can be used to control high performance aircraft and military aircraft based on sensor data indicating an unsafe condition of the pilot. For example, where the sensor data indicates that the pilot (under the current flight trajectory) will be exposed or is being exposed to a high stress conduction (e.g., excessive G forces as a result of an aerial maneuver) that is likely to cause the pilot to black out or become injured, a control system within the aircraft can modify the flight path and or speed of the aircraft to reduce the stress and avoid harm to the pilot and the aircraft.

In accordance with some embodiments, the system according to the invention can be used to monitor the performance of teams of people or subjects (e.g., dog sled teams or horse teams). In this embodiment, each member of the team can wear one or more sensing devices 110 that generate sensor data for each member of the team. The sensor data can be transmitted to an external hub 130 worn by one or more members of the team or positioned sufficiently near the field of play to receive the sensor data. The external hub 130 can aggregate the sensor data for each member of the team and determine one or more condition metrics for each member of the team. The coaching staff can use this information for player selection and substitution during an athletic contest. For example, by monitoring heart rate recovery, the system can rank each member of the team to identify those members of the team exhibiting the least level of fatigue at any point during an athletic contest, thereby enabling the coaching staff to determine which players to utilize during the duration.

In accordance with some embodiments of the invention, the system can be used with a head impact detection system, such as the Checklight product (Reebok, Canton, Mass.), which determines a level of head impact and provides an indication of a possible concussion. The system can use a conformable sensing device 110 worn on the chest and produce sensor data that can be used to determine heart rate, heart rate recovery, and respiration. The system can collect and store sensor data prior to head impact and compare the sensor data after the head impact to determine an indication of the severity of the impact and potential injury.

In accordance with some embodiments of the invention, the system can be used for pain management. There are many treatment options available for the management of chronic pain, one of which is spinal cord stimulation (SCS). A spinal cord stimulator is an implantable device used to exert pulsed electrical signals to the spinal cord to control chronic pain. The sensing device 110 can monitor physiologic and biologic parameters that are indicative of the pain the person or subject is suffering, including but not limited to, daily activities, sleep disturbances captured by EEG or ECG signals, respiration rate variability, heart rate variability, and posture. See, e.g., A. Paraschiv-Ionescu, et al., Scientific Reports (2013), 3, Article number: 2019, which is hereby incorporated by reference. When one or more physiologic and biologic parameters that are indicative of the pain the person or subject is suffering are detected by the sensing device 110, the sensing device 110 or external hub 130 could control the spinal cord stimulator to exert pulsed electrical signals to the spinal cord.

In accordance with some embodiments of the invention, the system can be used on a person or subject having refractory hypertension (i.e., resistant hypertension). The system can include an implantable device called Rheos Baroreflex Hypertension Therapy for the treatment of refractory hypertension. The sensing device 110 can measure activity level, sleep disturbances, fluid retention in the limbs and pulmonary edema caused by kidney regulation complications, e.g., by bioimpedance measurements (excitatory input stimulus and impedance measurement across the muscle/skin). Bioimpedance measurements can be conducted at high frequencies in the 50 kHz regime. See, e.g., M. Y. Jaffrin, et al., Medical Engineering & Physics (2008), 30, 1257-1269, which is hereby incorporated by reference. The data obtained by the sensing device 110 can be mapped over the therapy regimen to determine when the person or subject is experiencing poor hypertension, high heart rate, poor mobility vs good mobility relative to their medication cycles. This information can be tracked hourly, daily and nightly and retrospectively used by the doctors as insight to modify the treatment regimen by the implantable over time.

In accordance with some embodiments of the invention, the system can be used on a person or subject having diabetes neuropathy. The system can include an implantable device 170 called the metabolic neuromodulation system can help regulate blood glucose levels by delivering low-level radiofrequency energy through the wall of the blood vessel to the kidneys to disrupt the nerves that lead to the kidneys. The sensing device 110 can measure activity levels, sleep disturbances, fluid retention in the limbs and pulmonary edema caused by cardiac complications, e.g., by bioimpedance measurements. An AC signal applied at a set frequency (eg. 50 kHz) can be injected between two stimulating electrodes over a region of interest. Two separate recording electrodes positioned between these stimulating electrodes can then measure the complex impedance in this region as a way to assess the overall fluid vs tissue impedance profile. The presence of higher amount of fluid would be reflected in the complex impedance measurements. The data obtained by the sensing device 110 can be mapped over their therapy regimen to determine when the person or subject is experiencing poor mobility vs good mobility relative to the medication cycles and glucose levels. This information can be tracked hourly, daily, and nightly and retrospectively used by the doctors as insight to modify the treatment regimen by the metabolic neuromodulation system over time. Cardiac complications may result from disruptions in neural pathways caused by diabetes neuropathy. The nerves that innervate the heart may be disrupted resulting in abnormal heart rates and changes in blood pressure. Neuromodulation therapies in conjunction with cardiac and mobility monitoring thus provide a closed-loop solution for tracking these patients.

In accordance with some embodiments of the invention, the system can be used on a person or subject having traumatic brain injury. The system can include an implantable device that can provide electrical stimulation to the tongue that directly stimulates two cranial nerve nuclei (Trigeminal and Facial Nerve Nuclei) will excite neural impulses to the brainstem and cerebellum. This is referred to as cranial nerve non-invasive neuromodulation (CN-NINM). The activation of these structures induces neuroplasticity when combined with specific physical, cognitive and/or mental exercises, promoting recovery of selected functional damage in the brain such as problems with balance or walking. The sensing device 110 can measure activity level, balance, walking, stride length, gait, posture, sleep disturbances captured by EEG, ECG, or respiration or heart rate variability. The data obtained by the sensing device 110 can be mapped over their therapy regimen to determine when the person or subject is experiencing headaches, poor mobility/balance vs good mobility relative to the medication cycles. This information can be tracked hourly, daily, and nightly and retrospectively used by the doctors as insight to modify the treatment regimen by the implantable device over time.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

The system of the invention can be used to assist a person or subject having essential tremor. Totally Implantable Deep Brain Stimulation System in the ventral intermediate (VIM) nucleus of the thalamus can be implanted for the treatment of tremor due to essential tremor (e.g., the Libra System in the St. Jude Medical Deep Brain Stimulation System).

One or more sensing devices can be used to monitor action tremor, resting tremor, and daily movements. Each of the one or more sensing devices can include an accelerometer.

The one or more sensing devices are skin-coupled to the top of wrist, forearm, and top surface of hand. The device is in low power mode with accelerometer sensor set to detect tremors (3-10 Hz oscillations of the hand) based on set features (frequency and amplitude) while the subject is going about daily activity. Tremors, daily movements, and resting tremor are all catalogued by the sensor for 24-72 hours of continuous monitoring. Once the at least one sensing device is synced with an external smart device via Bluetooth low energy, this tremor information and duration of time the patient experienced tremors is all uploaded to the cloud where it is related to other sensor information collected from other sensing devices or to phone data collected about GPS, weather conditions, calendar activities, medication schedule, etc. for more in depth analytics.

Example 2

The system of the invention can be used to assist a person or subject having Parkinson's disease. Medical therapy is the mainstay of treatment for patients with Parkinson's disease (PD). After several years of drug therapy, however, a large proportion of patients experience worsening of their Parkinsonism and develop incapacitating motor fluctuations and dyskinesias. To solve this problem, attention has been directed to surgical procedures, such as deep brain stimulation (DBS). Recently, stimulating the areas of the brain that control movement, the globus pallidus (Gpi) and subthalamic nucleus (STN), has been proposed as a therapy for treating many of the disabling symptoms associated with PD and drug-induced side effects.

One or more sensing devices can be used to monitor daily activities, sleep, vitals (HR, HRV, resp), muscle potentials, range of motion, or stride length. Each of the one or more sensing devices can include at least one of: an accelerometer, electrodes, and a gyroscope.

The one or more sensing devices are skin-coupled to several body locations including the chest, forearms, shin, forehead, and tibialis anterior. The patient biometrics are tracked continuously and uploaded to cloud at night time and in the morning after waking up. The data is mapped over their therapy regimen to determine when they are experiencing poor mobility vs good mobility relative to their medication cycles. This information is tracked daily and nightly and retrospectively used by the doctors to modify the treatment regimen over time. It is thus important to view all of the data over several days, weeks and months for each individual in the context of daily and nightly uploaded biometric data and to visualize delta changes in the tremor, gait, balance and sleep disturbance features over time.

Example 3

The system of the invention can be used to assist a person or subject having overactive bladder. Sacral Neuromodulation, delivered by the Interstim® System, is indicated for patients who have failed or could not tolerate more conservative treatments for one or more of the following conditions: overactive bladder, urgency frequency, non-obstructive urinary retention, and chronic fecal incontinence.

One or more sensing devices can be used to monitor daily activities, sleep, and voiding. The one or more sensing devices can be mounted on the chest, forehead, and abdomen. Each of the one or more sensing devices can include at least one of: an accelerometer, electrodes, and a microphone.

The one or more sensing devices are worn during nighttime, right before bed. The patient's movement data is most important to track the number of voiding events (i.e., how often the patient gets up to go use the restroom). Placing a beacon in the bathroom allows the physician to know for certain that the patient gets up to use the restroom instead of going to the kitchen. The additional pieces of information that are interesting to measure include the voiding duration based on a microphone or EMG signals collected from a sensing device located at the mid-section. Sleep quality is also important to track over the course of a night, and to be able to track over several nights, weeks, and months to track progression. All of the multi-day tracking would require analysis in the cloud since uploads of data would happen in the morning after the patient awakes. The chest sensors are used to track sleep quality and the duration of time the patient is in rem, deep sleep or light sleep.

Example 4

The system of the invention can be used to assist a person or subject having chronic pain. For patients who fail some of the more conservative pharmacotherapies, the remaining option is limited to spinal cord stimulation (SCS), proven to be an effective therapy to more than half of those failing conservative treatments. Over 50% of those who have failed these more conservative methods of pain management, can now, under the guidance of a clinician utilizing SCS, have their pain levels successfully managed. SCS is a less invasive therapy that is a reversible treatment with greater long-term benefits than more permanent, radical approaches and one that deserves greater consideration in the management of chronic, intractable pain. One example of SCS devices is the Advanced Bionics totally implantable Spinal Cord Stimulation (SCS) System, the Stimulus System. This system is indicated as an aid in the management of chronic intractable pain of the trunk and/or limbs, including unilateral or bilateral pain associated with the following: failed back surgery syndrome, intractable low back pain and leg pain.

One or more sensing devices can be mounted on the chest. Each of the one or more sensing devices can include an accelerometer and/or electrodes. Similar to Example 3, the patient's sleep quality is tracked nightly based on resp, HR, HRV, roll over frequency. In addition to sleep, activity level and posture are tracked and uploaded to the cloud at night time. The data uploaded to the cloud is then compared to the smartphone data on GPS, weather, calendar of events, and schedule for medication in order to track changes in the patient's health over time (e.g., a day or more, several weeks, several months).

Example 5

The system of the invention can be used to assist a person or subject having hypertension. Rheos Baroreflex Hypertension Therapy System is an implantable device currently in clinical trial to treat patients with refractory hypertension.

One or more sensing devices are used to monitor activity level, sleep disturbances. In addition, a sensing device can measure fluid retention in the limbs and pulmonary edema caused by kidney regulation complications through bioimpedance measurements (excitatory input stimulus and impedance measurement across the muscle/skin). Bioimpedance measurements can be conducted at high frequencies in the 50 kHz regime. Each of the one or more sensing devices can include at least one of: an accelerometer, electrodes, and a PZT/strain gauge.

The one or more sensing devices are skin-coupled to several body locations including the chest, forearms, ankle, and tibialis anterior. The patient biometrics are tracked continuously and uploaded to cloud at night time and in the morning after waking up. The data is mapped over their therapy regimen to determine when they are experiencing poor hypertension, high heart rate, and poor mobility vs good mobility relative to their medication cycles. This information is tracked daily and nightly and retrospectively used by the doctors as insight to modify the treatment regimen over time.

Example 6

The system of the invention can be used to assist a person or subject having diabetes neuropathy. An implantable medical device called the Metabolic Neuromodulation System can be used to treat Type 2 Diabetes Mellitus (T2DM). The medical device delivers low-level radiofrequency energy through the wall of the blood vessel to the liver to disrupt the nerves that lead to the liver.

One or more sensing devices are used to monitor activity level, sleep disturbances. In addition, a sensing device can measure fluid retention in the limbs and pulmonary edema caused by cardiac complications through bioimpedance measurements with excitatory input stimulus and impedance measurement across the muscle/skin. Bioimpedance measurements can be conducted at high frequencies in the 50 kHz regime. Each of the one or more sensing devices can include at least one of: an accelerometer, electrodes, and a PZT/strain gauge.

The one or more sensing devices are skin-coupled to several body locations including the chest, forearms, ankle, and tibialis anterior. The patient biometrics are tracked continuously and uploaded to cloud at night time and in the morning after waking up. The data is mapped over their therapy regimen to determine when they are experiencing poor mobility vs good mobility relative to their medication cycles and glucose levels. This information is tracked hourly, daily and nightly and retrospectively used by the doctors as insight to modify the treatment regimen over time.

Example 7

The system of the invention can be used to assist a person or subject suffering from traumatic brain injury. Electrical stimulation to the tongue that directly stimulates two cranial nerve nuclei (Trigeminal and Facial Nerve Nuclei), will excite neural impulses to the brainstem and cerebellum. This is referred to as cranial nerve non-invasive neuromodulation (CN-NINM). The activation of these structures induces neuroplasticity when combined with specific physical, cognitive and/or mental exercises, promoting recovery of selected functional damage such as problems with balance or walking.

One or more sensing devices can be used to monitor activity level, balance, walking, stride length, gait, sleep disturbances captured by EEG, ECG, Resp/HRV, and posture. Each of the one or more sensing devices can include at least one of: an accelerometer, electrodes, and a gyroscope.

The one or more sensing devices are skin-coupled to several body locations including the chest, forehead, forearms, ankle, and tibialis anterior. The patient biometrics are tracked continuously and uploaded to cloud at night time and in the morning again after waking up. The data is mapped over their therapy regimen to determine when they are experiencing headaches, poor mobility/balance vs good mobility relative to their medication cycles. This information is tracked daily and nightly and retrospectively used by the doctors as insight to modify the treatment regimen over time.

Example 8

The system of the invention can be used to assist a person or subject having Multiple Sclerosis (MS). It is hypothesized that electrical stimulation to the tongue that directly stimulates two cranial nerve nuclei (Trigeminal and Facial Nerve Nuclei), will excite neural impulses to the brainstem and cerebellum. The activation of these structures induces neuroplasticity when combined with specific physical exercises, can reduce symptoms of advanced MS, targeting primarily postural stability (sitting and standing), upper extremity movement, and ability to perform self-transfers.

One or more sensing devices can be used to monitor activity level, balance, walking, stride length, gait, sleep disturbances captured by EEG, ECG, Resp/HRV, and posture. Each of the one or more sensing devices can include at least one of: an accelerometer, electrodes, and a gyroscope.

The one or more devices are skin-coupled to several body locations including the chest, forearms, forehead, ankle, and tibialis anterior. The patient biometrics are tracked continuously and uploaded to cloud at night time and in the morning again after waking up. The data is mapped over their therapy regimen to determine when they are experiencing relapses, poor mobility/balance vs good mobility relative to their medication cycles for MS. This information is tracked daily or maybe even once a week by physicians, and retrospectively used by doctors as insight to modify the treatment regimen over time.

Example 9

The system of the invention can be used to assist a person or subject having a cardiac disease. Electrical stimulation of the spine is being evaluated as a way to improve clinical signs and symptoms of heart failure. Neurostimulation uses an implantable pulse generator (IPG), or neurostimulator, similar to a cardiac pacemaker, with a lead, or thin wire, connecting the device to the spinal cord to deliver low-intensity electrical pulses. The procedure includes percutaneous placement of the leads in the spinal column and the stop-watch-sized neurostimulator is typically implanted in the abdomen.

One or more sensing devices can be used to monitor activity level, sleep disturbances, heart Rate, HRV. In addition, a sensing device can measure fluid retention in the limbs and pulmonary edema caused by cardiac complications through bioimpedance measurements with excitatory input stimulus and impedance measurement across the muscle/skin. Bioimpedance measurements can be conducted at high frequencies in the 50 kHz regime. Each of the one or more sensing devices can include at least one of: an accelerometer, electrodes, and a PZT/strain gauge.

The one or more sensing devices are skin-coupled to several body locations including the chest, forearms, forehead, ankle, and tibialis anterior. The patient biometrics are tracked continuously and uploaded to cloud at night time and in the morning again after waking up. If the heart rate data goes out of the "normal range" expected for the therapy to be effective, then a note is made to the physician on the data dashboard, with information on patient performance over several days, weeks and months.

The following references are incorporated herein by reference:

1. Heldman, D. A., Jankovic, J., Vaillancourt, D. E., Prodoehl, J., Elble, R. J., & Giuffrida, J. P. (2011). Essential tremor quantification during activities of daily living. Parkinsonism & Related Disorders, 17(7), 537-542.
2. Patel, S., Lorincz, K., Hughes, R., Huggins, N., Growdon, J., Standaert, D., et al. (2009). Monitoring Motor Fluctuations in Patients With Parkinson's Disease Using Wearable Sensors. IEEE Transactions on Information Technology in Biomedicine, 13(6), 864-873.
3. Eskofier, B. M., Paulus, J., Paulsen, U., Burkart, M., Wullich, B., & Huppert, V. (2014). An ambulatory sensor-based system for quantification of nighttime micturition for accurate nocturia assessment (pp. 566-569). Presented at the Engineering in Medicine and Biology Society (EMBC), 2014 36th Annual International Conference of the IEEE, IEEE.
4. Paraschiv-Ionescu, A., Buchser, E., & Aminian, K. (2013). Unraveling dynamics of human physical activity patterns in chronic pain conditions. Scientific Reports, 3.
5. C. Dagdeviren, Y. Su, P. Joe, R. Yona, Y. Liu, Y.-S. Kim, Y. Huang, A. R. Damadoran, J. Xia, L. W. Martin, Y. Huang and J. A. Rogers, "Conformable Amplified Lead Zirconate Titanate Sensors With Enhanced Piezoelectric Response for Cutaneous Pressure Monitoring," Nature Communications DOI: 10.1038/ncomms5496 (2014).
6. Jaffrin MY1, Morel H. (2008) Body fluid volumes measurements by impedance: A review of bioimpedance spectroscopy (BIS) and bioimpedance analysis (BIA) methods. Med Eng Phys.

What is claimed is:

1. A system comprising:
a sensing device having at least one sensor configured to sense at least one condition of a person in an environment, the sensing device including at least two rigid device islands, the at least two device islands coupled to each other via a flexible interconnect, one of the at least two rigid device islands including an electrode of the at least one sensor, the sensing device adaptable for contact to the skin of a person;
an external hub in communication with the sensing device and configured to receive sensor data from the sensing device; and
a therapeutic device configured to deliver therapy to the person upon receiving sensor data from the sensing device, the therapeutic device being physically separated from the sensing device and in wireless communication with the external hub or the sensing device.

2. The system according to claim 1, wherein the therapeutic device includes an electrical or chemical actuator.

3. The system according to claim 1, wherein the therapeutic device is configured to be placed in contact with a tissue of the person.

4. The system according to claim 3, wherein the therapeutic device is in contact with an internal organ of the person.

5. The system according to claim 4, wherein the therapeutic device is an implantable device.

6. The system according to claim 3, wherein the therapeutic device is configured to be placed in contact with the skin of the person.

7. The system according to claim 1, wherein the therapeutic device controls at least one of electrical stimulation, drug delivery, ultrasound stimulation, photostimulation, and thermal stimulation.

8. The system according to claim 1, wherein the sensing device includes at least one of: an accelerometer, a temperature sensor, a gyroscope, a light sensor, an ExG sensor, a sound sensor, and one or more electrodes.

9. The system according to claim 1, wherein the sensing device includes a processor, a memory, and/or a battery.

10. The system according to claim 1, wherein the at least one condition of the person is selected from the group consisting of activity level, heart rate, heart rate variability, respiration rate, respiration rate variability, skin temperature, core temperature, blood pressure, gait, posture, muscle potential, range of motion, stride length, and sleep quality.

11. The system according to claim 1, wherein the external hub is a smartphone.

12. The system according to claim 1, further comprising a target device in communication with the external hub and configured to receive signals from the hub that result in a change in operation of the target device.

13. The system according to claim 12, wherein the target device controls at least one of temperature, humidity, illumination or sound in the environment.

14. The system according to claim 1, wherein the at least two device islands and the flexible interconnect are encapsulated in a stretchable material.

* * * * *